US008519110B2

(12) United States Patent
Kowalska et al.

(10) Patent No.: US 8,519,110 B2
(45) Date of Patent: Aug. 27, 2013

(54) MRNA CAP ANALOGS

(75) Inventors: Joanna Kowalska, Radom (PL); Jacek Jemielity, Warsaw (PL); Edward Darzynkiewicz, Warsaw (PL); Robert E. Rhoads, Shreveport, LA (US); Maciej Lukaszewicz, Warsaw (PL); Joanna Zuberek, Warsaw (PL)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 195 days.

(21) Appl. No.: 12/996,243

(22) PCT Filed: Jun. 4, 2009

(86) PCT No.: PCT/US2009/046249
§ 371 (c)(1),
(2), (4) Date: Dec. 3, 2010

(87) PCT Pub. No.: WO2009/149253
PCT Pub. Date: Dec. 10, 2009

(65) Prior Publication Data
US 2011/0092574 A1 Apr. 21, 2011

(30) Foreign Application Priority Data
Jun. 6, 2008 (PL) ........................................ 385388

(51) Int. Cl.
*C12Q 1/68* (2006.01)
*C12N 15/00* (2006.01)
*C07H 21/02* (2006.01)
*C07H 21/04* (2006.01)

(52) U.S. Cl.
USPC ........... 536/23.1; 536/24.1; 435/6.1; 435/440

(58) Field of Classification Search
None
See application file for complete search history.

(56) References Cited

U.S. PATENT DOCUMENTS

| | | | |
|---|---|---|---|
| 6,262,036 B1 | 7/2001 | Arnold, Jr. et al. | 514/44 A |
| 7,074,596 B2 | 7/2006 | Darzynkiewicz et al. | 435/90 |
| 2006/0252115 A1 | 11/2006 | Darzynkiewicz et al. | 435/68.1 |
| 2006/0287271 A1 | 12/2006 | Fischer et al. | 514/44 |

OTHER PUBLICATIONS

Xu et al., Drug Delivery Trends in Clinical Trials and Translational Medicine: Challenges and Opportunities in the Delivery of Nucleic Acid-Based Therapeutics; J Pharmaceutical Sciences, vol. 100, No. 1, pp. 38-52, 2011.*
Kowalska, Joanna et al., "Synthesis and Properties of Boranophosphate mRNA Cap Analogues," Chemistry of Nucleic Acid Components, ed. M. Hocek, Collection Symposium Serial, vol. 10, pp. 383-385 (2008).
Kowalska, Joanna et al., "The First Examples of mRNA Cap Analogs Bearing Boranophosphate Modification," Nucleic Acids Symposium Series No. 52, pp. 289-290 (2008).
Cai, A. et al., "Quantitative assessment of mRNA cap analogues as inhibitors of in vitro translation," Biochemistry, vol. 38, pp. 8538-8547 (1999).
Carrasco, N. et al., "Efficient enzymatic synthesis of phosphoroselenoate RNA by using adenosine 5'-(-P-seleno)triphosphate," Angew. Chem. Int. Ed., vol. 45, pp. 94-97 (2006).
Carrasco, N. et al., "Enzymatic synthesis of phosphoroselenoate DNA using thymidine 5'-( -P-seleno)triphosphate and DNA polymerase for x-ray crystallography via MAD," J. Am. Chem. Soc., vol. 126, pp. 448-449 (2004).
De Benedetti, A. et al., "eIF-4E expression and its role in malignancies and metastases," Oncogene, vol. 23, pp. 3189-3199 (2004).
Graff, J.R. et al., "Therapeutic suppression of translation initiation factor eIF4E expression reduces tumor growth without toxicity," J. Clin. Investigation, vol. 117, pp. 2638-2648 (2007).
Grudzien, E. et al., "Differential inhibition of mRNA degradation pathways by novel cap analogs," J. Biol. Chem., vol. 281, pp. 1857-1867 (2006).
Grudzien, E. et al., "Novel cap analogs for in vitro synthesis of mRNAs with high translational efficiency," RNA, vol. 10, pp. 1479-1487 (2004).
Grudzien-Nogalska, E. et al., "Phosphorothioate cap analogs stabilize mRNA and increase translational efficiency in mammalian cells," RNA, vol. 13, pp. '745-1755 (2007).
Grudzien-Nogalska, E. et al., "Synthesis of Anti-Reverse Cap Analogs (ARCAs) and their Applications in mRNA Translation and Stability," Methods in Enzymology, vol. 431, pp. 203-227 (2007).
Herbert, T., "Rapid induction of apoptosis by peptides that bind initiation factor eIF4E," Curr. Biol., vol. 10, pp. 793-796 (2000).
Jemielity, J. et al., "Novel 'anti-reverse' cap analogues with superior translational properties," RNA, vol. 9, pp. 1108-1122 (2003).
Kowalska, J. et al., "Synthesis and characterization of mRNA cap analogs containing phosphorothioate substitutions that bind tightly to eIF4E and are resistant to the decapping pyrophosphatase DcpS," RNA, vol. 14, pp. 1119-1131 (2008).
Li, P. et al., "Nucleoside and oligonucleoside boranophosphates: chemistry and properties," Chem. Rev., vol. 107, pp. 4746-4796 (2007).
Li, P. et al., "Synthesis of -P-modified nucleoside diphosphates with ethylenediamine," J. Am. Chem. Soc., vol. 127, pp. 16782-16783 (2005).

(Continued)

*Primary Examiner* — Celine Qian
*Assistant Examiner* — Addison D Ault
(74) *Attorney, Agent, or Firm* — John H. Runnels

(57) ABSTRACT

Dinucleotide cap analogs are disclosed, modified at different phosphate positions with a boranophosphate group or a phosphoroselenoate group. The analogs are useful as reagents in the preparation of capped mRNAs and have increased stability both in vitro and in vivo. They may be used as inhibitors of cap-dependent translation. Optionally, the boranophosphate or phosphoroselenoate group has a 2'-O or 3'-O-alkyl group, preferably a methyl group, producing analogs called $BH_3$-ARCAs or Se-ARCAs. ARCAs may be modified with α-, β-, or γ-boranophosphate or phosphoroselenoate groups.

22 Claims, 15 Drawing Sheets

(56) References Cited

OTHER PUBLICATIONS

Misiura, K. et al., "Synthesis of nucleoside -thiotriphosphates via an oxathiaphospholane approach," Org. Lett., vol. 7, pp. 2217-2220 (2005).

Pallan, P.S. et al., "Selenium modification of nucleic acids: preparation of phosphoroselenoate derivatives for crystallographic phasing of nucleic acid structures," Nat. Protoc., vol. 2, pp. 640-646 (2007).

Shaw, B.R. et al., "Reading, Writing and Modulating Genetic Information with Boranophosphate Mimics of Nucleotides, DNA and RNA," Ann. N.Y. Acad. Sci., vol. 1201, pp. 23-29 (2003).

Stepinski, J. et al., "Synthesis and properties of mRNAs containing the novel "anti-reverse" cap analogues 7-methyl(3'-O-methyl)GpppG and 7-methyl(3'-deoxy)GpppG," RNA, vol. 7, pp. 1486-1495 (2001).

Summers, J. et al., "Boranophosphates as Mimics of Natural Phosphodiesters in DNA", Current Medicinal Chemistry, vol. 8, pp. 1147-1155 (2001).

Wild, J.s et al., "Selenium-assisted nucleic acid crystallography: use of phosphoroselenoates for MAD phasing of a DNA structure," J. Am. Chem. Soc., vol. 124, pp. 14910-14916 (2002); N. Carrasco et al. (2004); N. Carrasco et al. (2006).

* cited by examiner

A - Ap3G-LUC-polyA31
B - m$^7$Gp3G-LUC-polyA31
C - m$_2^{7,3'O}$Gp3G-LUC-polyA31
D - m$_2^{7,2'O}$Gpp$_S$pG(D1)-LUC-polyA31
E - m$_2^{7,2'O}$Gpp$_S$pG(D2)-LUC-polyA31
F - m$_2^{7,2'O}$Gpp$_{Se}$pG(D1)-LUC-polyA31
G - m$_2^{7,2'O}$Gpp$_{Se}$pG(D2)-LUC-polyA31
H - m$_2^{7,2'O}$Gpp$_{BH3}$pG(D1)-LUC-polyA31
I - m$_2^{7,2'O}$Gpp$_{BH3}$pG(D2)-LUC-polyA31
J - m$^7$Gpp$_{BH3}$pG(D1)-LUC-polyA31
K - m$^7$Gpp$_{BH3}$pm$^7$G-LUC-polyA31
L - m$_2^{7,2'O}$Gppp$_{BH3}$G(D1)-LUC-polyA31
M - m$_2^{7,2'O}$Gppp$_{BH3}$G(D2)-LUC-polyA31

| Cap Analog | Relative Slope |
|---|---|
| ARCA | 1.00 |
| BH3 (D1) | 1.64 |
| BH3 (D2) | 2.09 |
| S-ARCA (D2) | 2.01 |

MRNA CAP ANALOGS

The development of this invention was partially funded by the United States government under grant number R01GM20818 awarded by the National Institute of General Medical Sciences of the National Institutes of Health. The United States government has certain rights in this invention.

The development of this invention was partially funded by the Government of Poland under grant number PBZ-MNiSW-07/I/2007 awarded by the National Science Support Project 2008-2010.

This is the United States national stage of international application PCT/US2009/046249, international filing date Jun. 4, 2009. The benefit of the filing date of Polish patent application serial no. P 385388, filed Jun. 6, 2008 is claimed under 35 U.S.C. §119(a) and 365.

TECHNICAL FIELD

This invention pertains to new dinucleotide cap analogs and their uses, RNA molecules containing these analogs, the use of these analogs in RNA synthesis, the use of these analogs in peptide and protein synthesis, the use of these analogs to inhibit translation, and other uses.

BACKGROUND ART

Ribonucleic acid (RNA) is a single-stranded, linear polymer of nucleotides. Each nucleotide unit contains a nitrogenous base, a ribose sugar, and a phosphate group. There are several types of RNA molecules. Messenger RNA (mRNA) molecules are those whose nucleotide sequence determines the amino acid composition of proteins. In eukaryotes, the 5'-ends of most mRNAs are blocked, or "capped" with a modified guanine nucleotide. The cap contains a 5'-5' triphosphate linkage between two nucleosides and a 7-methyl group on a guanine ring distal to the RNA polymer chain. Some other forms of RNA are also capped, e.g., small nuclear RNAs (snRNAs). RNA capping regulates intracellular molecular activities, including RNA stability and translational efficiency.

The ability to synthesize capped RNA molecules in vitro is useful because it allows one to prepare RNA molecules that will function properly in a variety of biological applications. Such applications include both research applications and commercial production of polypeptides, e.g., producing in a cell-free translation system polypeptides containing an "unnatural" amino acid at a specific site, or producing in cultured cells polypeptides that require post-translational modification for activity or stability. Because capped RNA molecules are more stable and bind more readily to the cell's translational machinery, translation of capped RNAs proceeds for a considerably longer time than is the case for non-capped RNAs, resulting in greater production of protein.

The method most frequently used to make capped RNAs in vitro is to transcribe a DNA template with either a bacterial or bacteriophage RNA polymerase in the presence of all four ribonucleoside triphosphates and a cap dinucleotide such as m$^7$G(5')ppp(5')G (also called m$^7$GpppG). The RNA polymerase initiates transcription with a nucleophilic attack by the 3'-OH of the Guo moiety of m$^7$GpppG on the α-phosphate of the next templated nucleoside triphosphate, resulting in the intermediate m$^7$GpppGpN. The formation of the competing GTP-initiated product pppGpN is suppressed by setting the molar ratio of m$^7$GpppG to GTP between 5 and 10 in the transcription reaction mixture. The 5'-capped mRNAs produced with m$^7$GpppG can take either of two forms, one containing the cap analog incorporated in the correct, forward orientation [m$^7$G(5')ppp(5')GpNp . . . ], and one containing the analog in the reverse orientation [G(5')ppp(5')m$^7$Gp-Np . . . ]. The latter are not recognized as capped mRNAs by the cell's translational machinery and decrease the translational efficiency of synthetic mRNA preparations. This problem can be averted by the use of cap analogs that have O-methyl or deoxy modifications at either the C2' or C3' positions of m7Guo. See J. Stepinski et al., "Synthesis and properties of mRNAs containing the novel "anti-reverse" cap analogues 7-methyl(3'-O-methyl)GpppG and 7-methyl(3'-deoxy)GpppG," *RNA*, vol. 7, pp. 1486-1495 (2001); and J. Jemielity et al., "Novel 'anti-reverse' cap analogues with superior translational properties," *RNA*, vol. 9, pp. 1108-1122 (2003). These cap analogs are incorporated into RNA transcripts exclusively in the forward orientation and are therefore called "anti-reverse cap analogs" (ARCAs). In a rabbit reticulocyte lysate (RRL) translation system, ARCA-capped mRNAs had translational efficiencies that were two-fold higher than transcripts capped with m$^7$GpppG (Stepinski et al., 2001). In cultured mammalian cells, mRNAs capped with ARCAs are translated 2- to 2.5-fold more efficiently than those capped with m$^7$GpppG. See E. Grudzien et al., "Differential inhibition of mRNA degradation pathways by novel cap analogs," *J. Biol. Chem.*, vol. 281, pp. 1857-1867 (2006).

The amount of protein produced from synthetic mRNAs introduced into cultured mammalian cells is limited by the natural degradation of mRNA. One in vivo pathway for mRNA degradation begins with the removal of the mRNA cap. This removal is catalyzed by a heterodimeric pyrophosphatase, which contains a regulatory subunit (Dcp1) and a catalytic subunit (Dcp2). The catalytic subunit cleaves between the α and β phosphate groups of the triphosphate bridge.

E. Grudzien et al. (2006) described a cap analog, m$_2^{7,3'-O}$Gpp$_{CH2}$pG, in which a methylene group replaced the O atom between the α and β phosphate groups. mRNAs capped with this analog were resistant to hydrolysis by recombinant human Dcp2 in vitro. When introduced into cultured cells, mRNAs capped with the analog m$_2^{7,3'-O}$Gpp$_{CH2}$pG were more stable than those capped with m$_2^{7,3'-O}$GpppG. However, the mRNA capped with m$_2^{7,3'-O}$Gpp$_{CH2}$pG had lower overall translational efficiency, presumably because m$_2^{7,3'-O}$Gpp$_{CH2}$pG has a lower binding affinity for eIF4E than that of m$_2^{7,3'-O}$GpppG. The eukaryotic translation initiation factor eIF4E is involved in bringing the capped mRNA to the ribosome for translation.

J. Kowalska et al., "Synthesis and characterization of mRNA cap analogs containing phosphorothioate substitutions that bind tightly to eIF4E and are resistant to the decapping pyrophosphatase DcpS," *RNA*, vol. 14, pp. 1119-1131 (2008) described syntheses of three ARCAs in which one of the three non-bridging O atoms in the triphosphate chain was replaced with an S atom. Each of these phosphorothioate analogs (also called S-ARCAs) was synthesized as a mixture of diastereomers that could be separated chromatographically to make pure diastereomers. The binding affinity of the phosphorothioate cap analogs to eIF4E was equal to or, in some cases, greater than that of m$^7$GpppG.

E. Grudzien et al., "Phosphorothioate cap analogs stabilize mRNA and increase translational efficiency in mammalian cells," *RNA*, vol. 13, pp. 1745-1755 (2007) showed that mRNAs capped with S-ARCAs modified at the β phosphate were resistant to hydrolysis by recombinant human Dcp2 in vitro. Furthermore, mRNA capped with one β S-ARCA diastereomer had a longer half-life when introduced into mammalian cells than that of the corresponding ARCA-capped mRNA; and it also had a greater translational efficiency in cells. The first of these properties presumably resulted from the resistance of the β S-ARCA to hydrolysis by Dcp2, and the second property presumably resulted from the higher affinity of the β-S-ARCA for eIF4E.

Another use for synthetic mRNA cap analogs is to inhibit cap-dependent translation by competition with capped mRNA for binding to eIF4E. See A. Cai et al., "Quantitative assessment of mRNA cap analogues as inhibitors of in vitro translation," *Biochemistry*, vol. 38, pp. 8538-8547 (1999); and E. Grudzien et al., "Novel cap analogs for in vitro synthesis of mRNAs with high translational efficiency," *RNA*, vol. 10, pp. 1479-1487 (2004).

The ability of cap analogs to inhibit translation has potential therapeutic significance. Many types of cancer cells over-express eIF4E, which can lead to increased expression of proteins that promote oncogenesis and metastasis. See A. De Benedetti et al., "eIF-4E expression and its role in malignancies and metastases," *Oncogene*, vol. 23, pp. 3189-3199 (2004). Reducing eIF4E expression with siRNA, antisense oligonucleotides, or a specific eIF4E repressor can inhibit tumor growth and oncogenesis. See J. R. Graff et al., "Therapeutic suppression of translation initiation factor eIF4E expression reduces tumor growth without toxicity," *J. Clin. Investigation*, vol. 117, pp. 2638-2648 (2007); and T. Herbert, "Rapid induction of apoptosis by peptides that bind initiation factor eIF4E," *Curr. Biol.*, vol. 10, pp. 793-796 (2000). In addition, the translational activity of eIF4E can be suppressed by saturating the cells with competing, translationally deficient cap analogs.

Some synthetic cap analogs are specific inhibitors of eIF4E activity and are therefore potentially useful as agents for treating oncogenesis and metastasis, immunosuppression in organ transplantation, and other medical conditions. However, these potential uses for cap analogs have never previously been demonstrated in vivo, in part due to the instability of cap analogs in intracellular conditions.

J. Kowalska et al. (2008) demonstrated that γ-S-ARCAs are strong inhibitors of translation in a cell-free system, presumably due to their high binding affinity for eIF4E. The γ-modified analogs are resistant to hydrolysis by the human DcpS enzyme, which is a scavenger pyrophosphatase responsible for degradation of this type of compound.

Other modifications can help protect capped mRNA against enzymatic degradation. One example is a boranophosphate modification, in which one of the non-bridging O atoms is replaced with a borane group ($BH_3^-$) (sometimes called the $BH_3$-analogs). Another example is a phosphoroselenoate modification, in which one of the non-bridging O atoms is replaced with a selenium atom (sometimes called the Se-analogs). The phosphorothioate, boranophosphate, and phosphoroselenoate groups all replace non-bridging oxygen atoms and share some chemical and biochemical properties. However, there are also differences among these groups. For example, the P—X bond lengths differ (where X denotes S, Se, or $BH_3$), the van der Waals radii of the X groups differ, and the affinity of the X groups for various divalent and other metal cations differ. These differing chemical properties alter the biological activities of cap analogs with these groups, including their interactions with cap-binding proteins and their susceptibility to enzymatic degradation.

Boranophosphate mononucleotides and boranophosphate polyphosphate dinucleotides were reviewed by P. Li et al., "Nucleoside and oligonucleoside boranophosphates: chemistry and properties," *Chem. Rev.*, vol. 107, pp. 4746-4796 (2007).

Boranophosphate polyphosphate dinucleoside analogs are described in published patent application US2006/0287271, as are their use against diseases modulated by P2Y receptors, e.g., type 2 diabetes and cancer.

Boranophosphate nucleotide analogs have similarities with phosphorothioate analogs due to similar bond angles, $pK_a$ values, and P-diastereoisomerism. However, in some cases they are as much as 10-fold more resistant to enzymatic hydrolysis than their phosphorothioate counterparts. They are also more lipophilic than phosphorothioates, which may help them to penetrate cell membranes and reach intracellular translational machinery. Boranophosphate analogs can also be used in boron neutron capture therapy (BNCT). See B. R. Shaw et al., "Reading, Writing and Modulating Genetic Information with Boranophosphate Mimics of Nucleotides, DNA and RNA," *Ann. N.Y. Acad. Sci.*, vol. 1201, pp 23-29 (2003); and J. Summers et al., "Boranophosphates as Mimics of Natural Phosphodiesters in DNA", *Current Medicinal Chemistry*, vol. 8, pp 1147-1155 (2001).

Phosphoroselenoate analogs of nucleoside di- and triphosphates modified in the α position were described in K. Misiura et al., "Synthesis of nucleoside α-thiotriphosphates via an oxathiaphospholane approach," *Org. Lett.*, vol. 7, pp 2217-2220 (2005); P. Li et al., "Synthesis of α-P-modified nucleoside diphosphates with ethylenediamine," *J. Am. Chem. Soc.*, vol. 127, pp. 16782-16783 (2005); N. Carrasco et al., "Enzymatic synthesis of phosphoroselenoate DNA using thymidine 5'-(α-P-seleno)triphosphate and DNA polymerase for x-ray crystallography via MAD," *J. Am. Chem. Soc.*, vol. 126, pp. 448-449 (2004); and N. Carrasco et al., "Efficient enzymatic synthesis of phosphoroselenoate RNA by using adenosine 5'-(α-P-seleno)triphosphate," *Angew. Chem. Int. Ed.*, vol. 45, pp. 94-97 (2006). However, to the knowledge of the inventors, there have been no prior reports of nucleoside polyphosphate analogs modified in any position other than the α position, nor of dinucleoside polyphosphates modified at any position.

Phosphoroselenoate nucleotide analogs are similar to phosphorothioates and boranophosphates due to their similar bond angles, $pK_a$ values, P-diastereoisomerism, and resistance to enzymatic degradation. Phosphoroselenoates can be very useful in nucleic acid crystallography because Se can be used in the multi-wavelength anomalous dispersion (MAD) technique. See J. Wilds et al., "Selenium-assisted nucleic acid crystallography: use of phosphoroselenoates for MAD phasing of a DNA structure," *J. Am. Chem. Soc.*, vol. 124, pp 14910-14916 (2002); N. Carrasco et al. (2004); N. Carrasco et al. (2006); and P. S. Pallan et al., "Selenium modification of nucleic acids: preparation of phosphoroselenoate derivatives for crystallographic phasing of nucleic acid structures," *Nat. Protoc.*, vol. 2, pp. 640-646 (2007).

See also our work on anti-reverse cap mRNA analogs described in U.S. Pat. No. 7,074,596; and published international patent application WO 2008/157688.

SUMMARY OF THE INVENTION

We have discovered a new class of dinucleotide cap analogs. The novel dinucleotide cap analogs are modified at various phosphate positions with a boranophosphate group or a phosphoroselenoate group. The novel analogs have broad utility as reagents in the preparation of capped mRNAs. They have increased stability both in vitro and in vivo. They may be used as inhibitors of cap-dependent translation. Optionally, the boranophosphate or phosphoroselenoate group has a 2'-O or 3'-O-alkyl group, preferably a methyl group, producing analogs called $BH_3$-ARCAs or Se-ARCAs. ARCAs may be modified with α-, β-, or γ-boranophosphate or phosphoroselenoate groups. Selection of the type and location of modification modulates the activity of proteins that recognize the cap during synthesis, processing, nucleo-cytoplasmic export, translation, and degradation of mRNA.

Table 1 lists several $BH_3$-analogs and Se-analogs that have been or will be synthesized and characterized by chemical, biophysical, biochemical, and molecular biological methods. Compounds that are particularly favorable in mRNA caps include the β-$BH_3$-ARCAs and β-Se-ARCAs. Compounds that are particularly favorable as translation inhibitors include the β- and γ-$BH_3$-analogs and γ-Se-analogs.

TABLE 1

$BH_3$— and Se-analogs

| Compound name[a] | X | Y | Z | R | N[b] |
|---|---|---|---|---|---|
| $m^7Gppp_{BH3}G$ (D1) | $BH_3$ | O | O | H | Gua |
| $m^7Gppp_{BH3}G$ (D2) | $BH_3$ | O | O | H | Gua |
| $m^7Gpp_{BH3}pG$ (D1) | O | $BH_3$ | O | H | Gua |
| $m^7Gpp_{BH3}pG$ (D2) | O | $BH_3$ | O | H | Gua |
| $m^7Gpp_{BH3}pm^7G$ | O | $BH_3$ | O | H | $m^7Gua$ |
| $m^7Gp_{BH3}ppG$ (D1)[†] | O | O | $BH_3$ | H | Gua |
| $m^7Gp_{BH3}ppG$ (D2)[†] | O | O | $BH_3$ | H | Gua |
| $m_2^{7,2'-O}Gppp_{BH3}G$ (D1) | $BH_3$ | O | O | $CH_3$ | Gua |
| $m_2^{7,2'-O}Gppp_{BH3}G$ (D2) | $BH_3$ | O | O | $CH_3$ | Gua |
| $m_2^{7,2'-O}Gpp_{BH3}pG$ (D1) | O | $BH_3$ | O | $CH_3$ | Gua |
| $m_2^{7,2'-O}Gpp_{BH3}pG$ (D2) | O | $BH_3$ | O | $CH_3$ | Gua |
| $m_2^{7,2'-O}Gp_{BH3}ppG$ (D1)[†] | O | O | $BH_3$ | $CH_3$ | Gua |
| $m_2^{7,2'-O}Gp_{BH3}ppG$ (D2)[†] | O | O | $BH_3$ | $CH_3$ | Gua |
| $m^7Gppp_{Se}G$ (D1)[†] | Se | O | O | H | Gua |
| $m^7Gppp_{Se}G$ (D2)[†] | Se | O | O | H | Gua |
| $m^7Gpp_{Se}pG$ (D1)[†] | O | Se | O | H | Gua |
| $m^7Gpp_{Se}pG$ (D2)[†] | O | Se | O | H | Gua |
| $m^7Gpp_{Se}pm^7G$[†] | O | Se | O | H | $m^7Gua$ |
| $m^7Gp_{Se}ppG$ (D1) | O | O | Se | H | Gua |
| $m^7Gp_{Se}ppG$ (D2) | O | O | Se | H | Gua |
| $m_2^{7,2'-O}Gppp_{Se}G$ (D1)[†] | Se | O | O | $CH_3$ | Gua |
| $m_2^{7,2'-O}Gppp_{Se}G$ (D2)[†] | Se | O | O | $CH_3$ | Gua |
| $m_2^{7,2'-O}Gpp_{Se}pG$ (D1) | O | Se | O | $CH_3$ | Gua |
| $m_2^{7,2'-O}Gpp_{Se}pG$ (D2) | O | Se | O | $CH_3$ | Gua |
| $m_2^{7,2'-O}Gp_{Se}ppG$ (D1)[†] | O | O | Se | $CH_3$ | Gua |
| $m_2^{7,2'-O}Gp_{Se}ppG$ (D2)[†] | O | O | Se | $CH_3$ | Gua |

[a]D1 and D2 refer to diastereomers.
[b]Gua is guanine (Formula 2a) and $m^7$Gua is 7-methylguanine (Formula 2b, in which X is $CH_3$).
[†]Compounds that are expected to have favorable properties, but that had not yet been synthesized as of the international filing date of the present PCT application.

MODES FOR PRACTICING THE INVENTION

Synthesis and Isolation of Cap Analogs

The chemical synthesis of the boranophosphate and phosphoroselenoate cap analogs was a modification of reported synthetic schemes for other analogs. See M. Kadokura et al., "Efficient synthesis of γ-methyl-capped guanosine 5'-triphosphate as a 5'-terminal unique structure of U6 RNA via a new triphosphate bond formation involving activation of methyl phosphorimidazolidate using $ZnCl_2$ as a catalyst in DMF under anhydrous conditions," *Tetrahedron Lett.*, vol. 38, pp. 8359-8362 (1997); J. Stepinski et al. (2001); M. Kalek et al., "Enzymatically stable 5' mRNA cap analogs," *Bioorg. Med. Chem.*, vol. 14, pp. 3223-3230 (2006); and J. Kowalska et al. (2008).

A mononucleotide is converted to a reactive imidazolide derivative, which is then coupled to another mononucleotide in DMF in the presence of excess $ZnCl_2$. The $ZnCl_2$ significantly enhances the solubility of the reactants in organic solvents, inhibits hydrolysis of imidazolide derivatives, and accelerates the reaction rate. Other metal chlorides such as $MnCl_2$, $CdCl_2$ or $MgCl_2$ may also be used to mediate pyrophosphate bond formation, but are generally less efficient than $ZnCl_2$. See M. Kadokura et al., "Efficient synthesis of γ-methyl-capped guanosine 5'-triphosphate as a 5'-terminal unique structure of U6 RNA via a new triphosphate bond formation involving activation of methyl phosphorimidazolidate using $ZnCl_2$ as a catalyst in DMF under anhydrous conditions," *Tetrahedron Lett.*, vol. 38, pp. 8359-8362 (1997).

A generally similar synthetic scheme was used to synthesize cap analogs containing phosphate-boranophosphate and phosphate-phosphoroselenoate bonds. However, for boranophosphate analogs, best results were obtained using $MgCl_2$ rather than $ZnCl_2$ as the coupling mediator. In the presence of $ZnCl_2$, coupling reactions also occurred, but were accompanied by significant side-reactions related to P—$BH_3$ bond cleavage under the acidic conditions produced by $ZnCl_2$.

Figure 1:
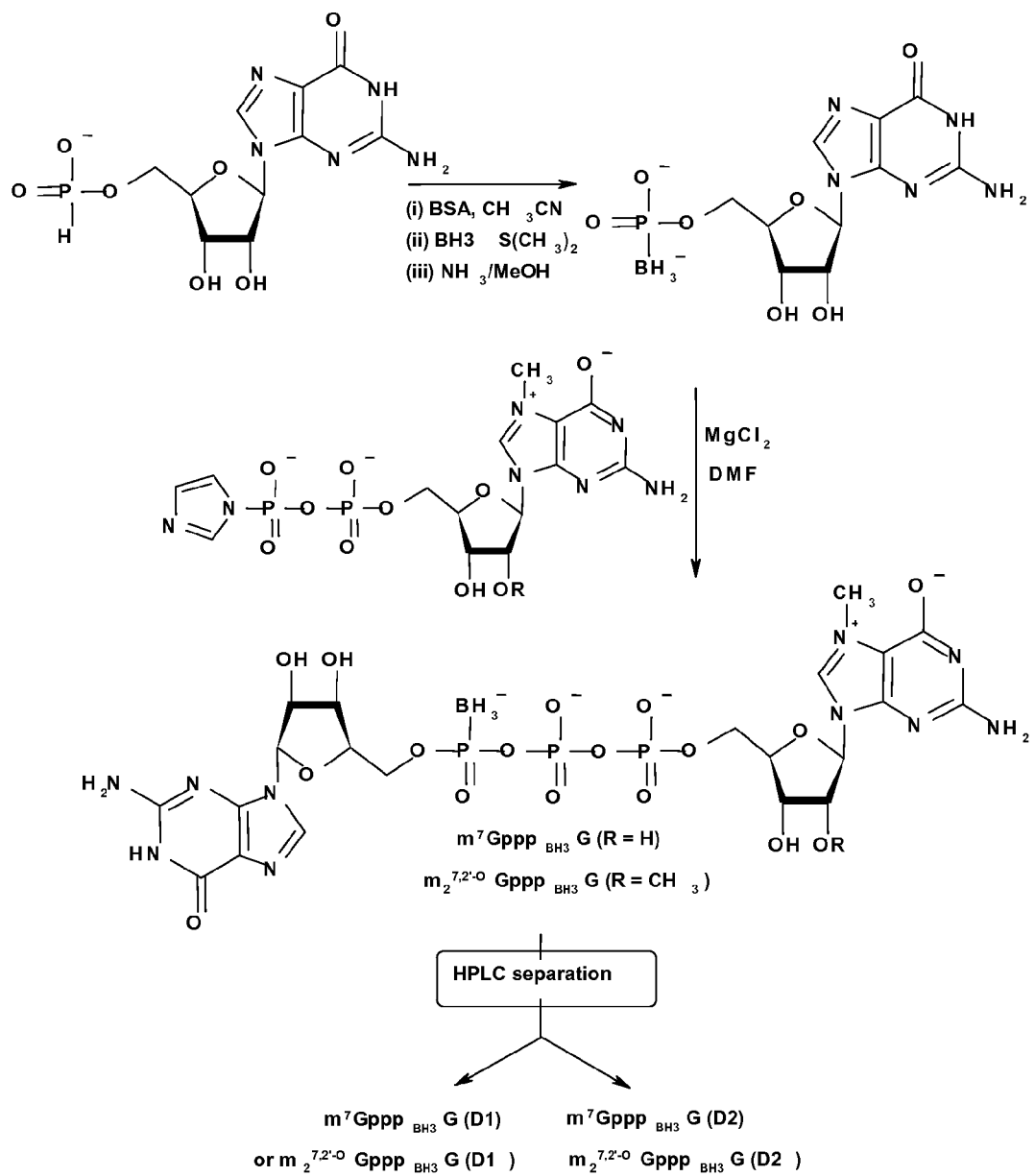
FIG. 1 depicts a synthesis of cap analogs with a boranophosphate group at the α-position of the 5',5'-triphosphate bridge.

FIG. 1 depicts the synthesis of analogs modified at the α-position. We first developed a method for the synthesis of the intermediate guanosine 5'-boranophosphate. Guanosine 5'-(H-phosphonate) was silated with N,O-bis(trimethylsilyl)acetamide (BSA). The resulting intermediate, bis(trimethylsilyl)phosphite, was boronated by treatment with a $BH_3.SMe_2$ complex, without isolation. Subsequent desilylation and purification by ion-exchange chromatography afforded the desired guanosine 5'-boranophosphate at ~30% yield. To obtain the cap analog $m^7Gpp_{BH3}G$, or its ARCA counterpart, $m_2^{7,2'-O}Gpp_{BH3}G$, guanosine 5'-boranophosphate was coupled with the imidazolide derivative of m⁷GDP or of $m_2^{7,2'-O}$GDP, respectively, in a 9:1 DMF/water mixture in the presence of excess $MgCl_2$. In both cases, the result was a mixture of two P-diastereomers that were then separated by reverse phase (RP) HPLC. The diastereomers were termed D1 and D2, accordingly to their elution order from the RP HPLC column.

Figure 2:
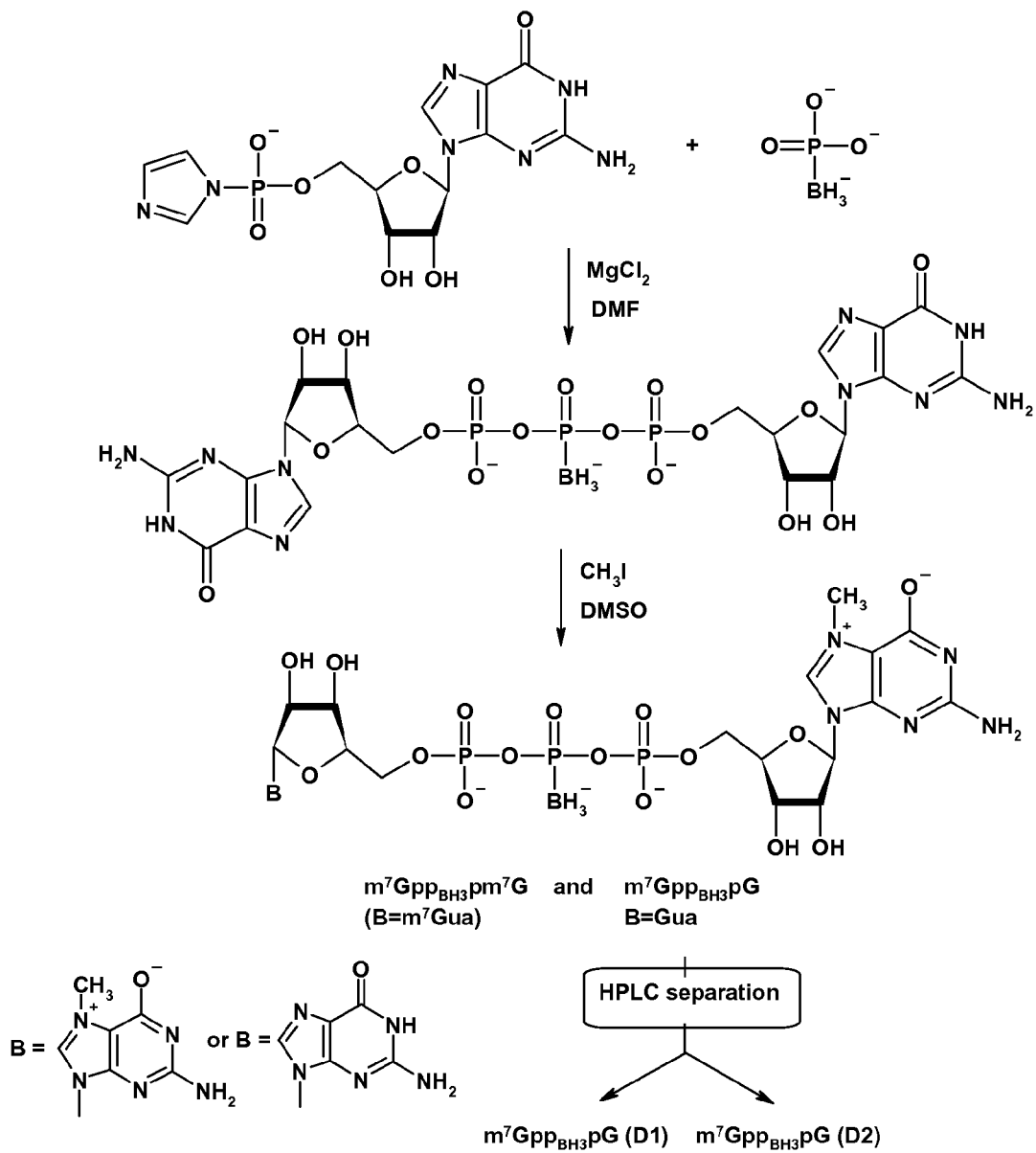
FIG. 2 depicts a synthesis of cap analogs with a boranophosphate group at the β-position of the 5',5'-triphosphate bridge.

FIG. 2 depicts the synthesis of analogs modified at the β-position. The boranophosphate triethylammonium salt was obtained by a modification of the procedure of V. Nahum et al., "Boranophosphate salts as an excellent mimic of phosphate salts: preparation, characterization, and properties," *Eur. J. Inorg. Chem.*, vol. 20, pp. 4124-4131 (2004). In the original procedure, tris(trimethylsilyl) phosphite was boronated with the $BH_3.SMe_2$ complex. Subsequent desililation in methanol in the presence of an appropriate base (e.g., ammonia, tributylamine, etc.), followed by evaporation to dryness, afforded the boranophosphate as the corresponding salt (ammonium, tributylammonium, etc.). However, the product was contaminated with the phosphonic acid salt (up to 20%). This contamination was probably the result of partial hydrolysis of tris(trimethylsilyl)phosphite to bis(trimethylsilyl)phosphite under reaction conditions that were not perfectly anhydrous (the bis compound did not undergo the subsequent boranation). We overcame this problem by adding excess silating reagent (BSA) to the reaction mixture, which inhibited formation of bis(trimethylsilyl)phosphite. The boranophosphate triethylammonium salt obtained in this way was coupled with excess guanosine monophosphate imidazolide derivative to produce a symmetrical diguanosine 5',5'"-(2-boranotriphosphate) ($Gpp_{BH3}pG$, FIG. 2).

Figure 3:
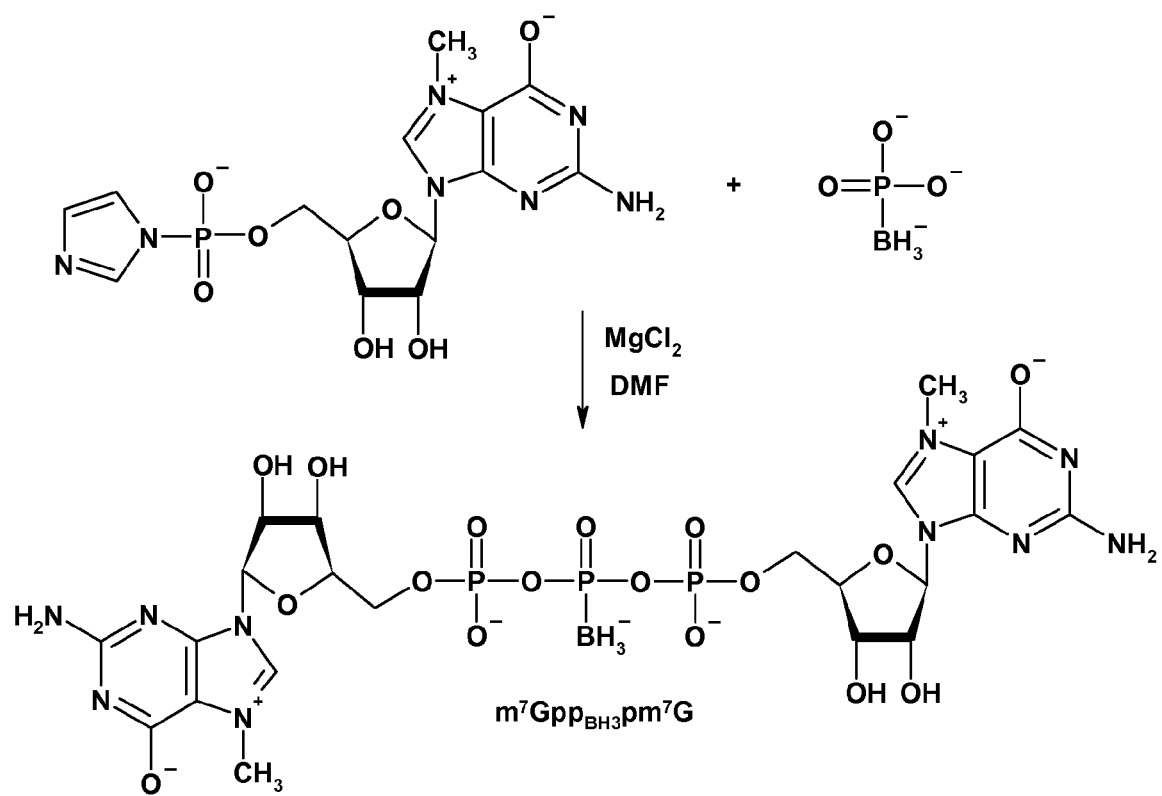
FIG. 3 depicts a synthesis of $m^7Gpp_{BH3}pm^7G$ (method II).

This compound was subsequently treated with methyl iodide in DMSO to introduce a methyl group at the guanosine N7 position. The reaction produced a mixture of monomethylated and dimethylated cap analogs ($m^7Gpp_{BH3}pG$ and $m^7Gpp_{BH3}pm^7G$). The ratio of these products can be controlled by adjusting the reaction conditions. In the presence of a ~4× excess of methyl iodide, $m^7Gpp_{BH3}pG$ was formed as a major product (~70% yield). With an ~8×-10× excess of methyl iodide, $m^7Gpp_{BH3}pm^7G$ was the predominant product (~50%). However, a preferred route to the latter product was to couple boranophosphate with a 7-methylguanosine imidazolide derivative, which allowed us to isolate the product with 34% yield, but in a one-step synthesis. See FIG. 3.

Figure 4:
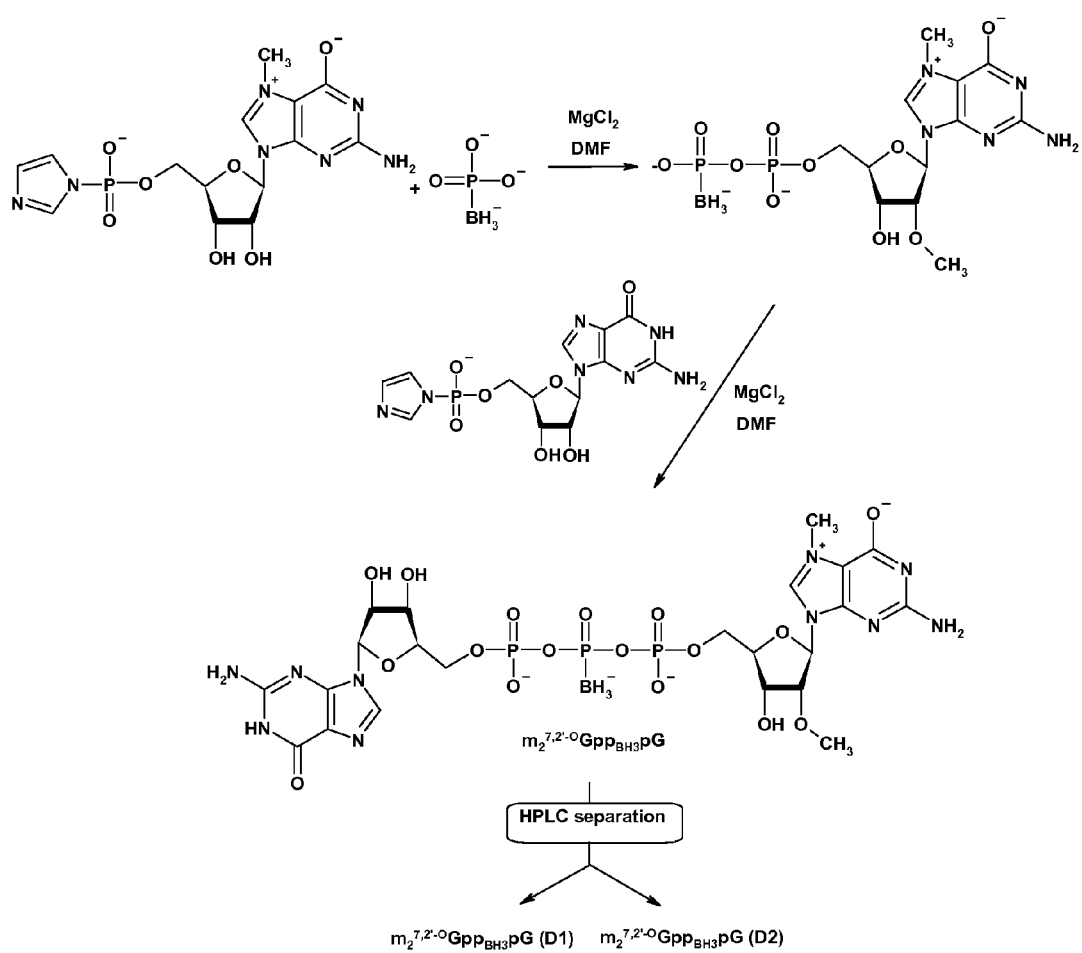
FIG. 4 depicts a synthesis of $m_2^{7,2'-O}Gpp_{BH3}pG$.

Initial attempts to obtain the intermediate 7,2'-O-dimethylguanosine 5'-(2-boranodiphosphate) ($m_2^{7,2'-O}GDP\beta BH_3$), useful for synthesis of β-$BH_3$-ARCAs ($m_2^{7,2'-O}Gpp_{BH3}pG$), showed poor success. We coupled $m_2^{7,2'-O}$GMP-Im and excess boranophosphate triethylammonium salt in the presence of $MgCl_2$. Although an MS ESI(−) analysis of the coupling products showed that the desired product had been formed, it was not possible to isolate it in sufficient amounts. The compound may undergo relatively fast hydrolysis in aqueous solutions, making separation by ion-exchange chromatography practically impossible. So we developed an alternative synthesis of $m_2^{7,2'-O}Gpp_{BH3}pG$, by reacting $m_2^{7,2'-O}$GMP-Im with excess boranophosphate in the presence of $MgCl_2$ to produce $m_2^{7,2'-O}GDP\beta BH_3$, which then, without isolation, was coupled with excess GMP-Im. See FIG. 4.

Figure 5:
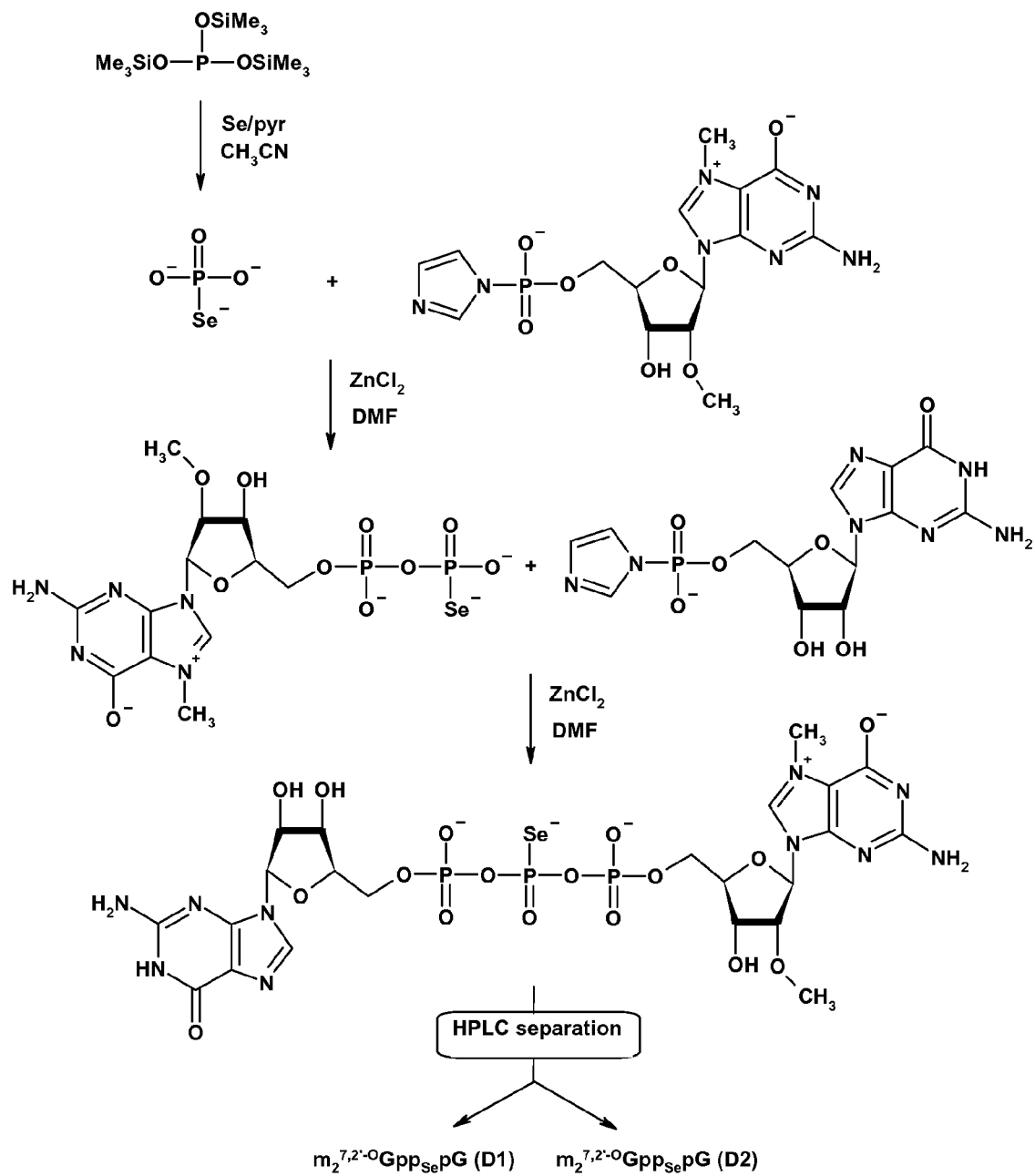
FIG. 5 depicts a synthesis of $m_2^{7,2'-O}Gpp_{Se}pG$.
Figure 6:
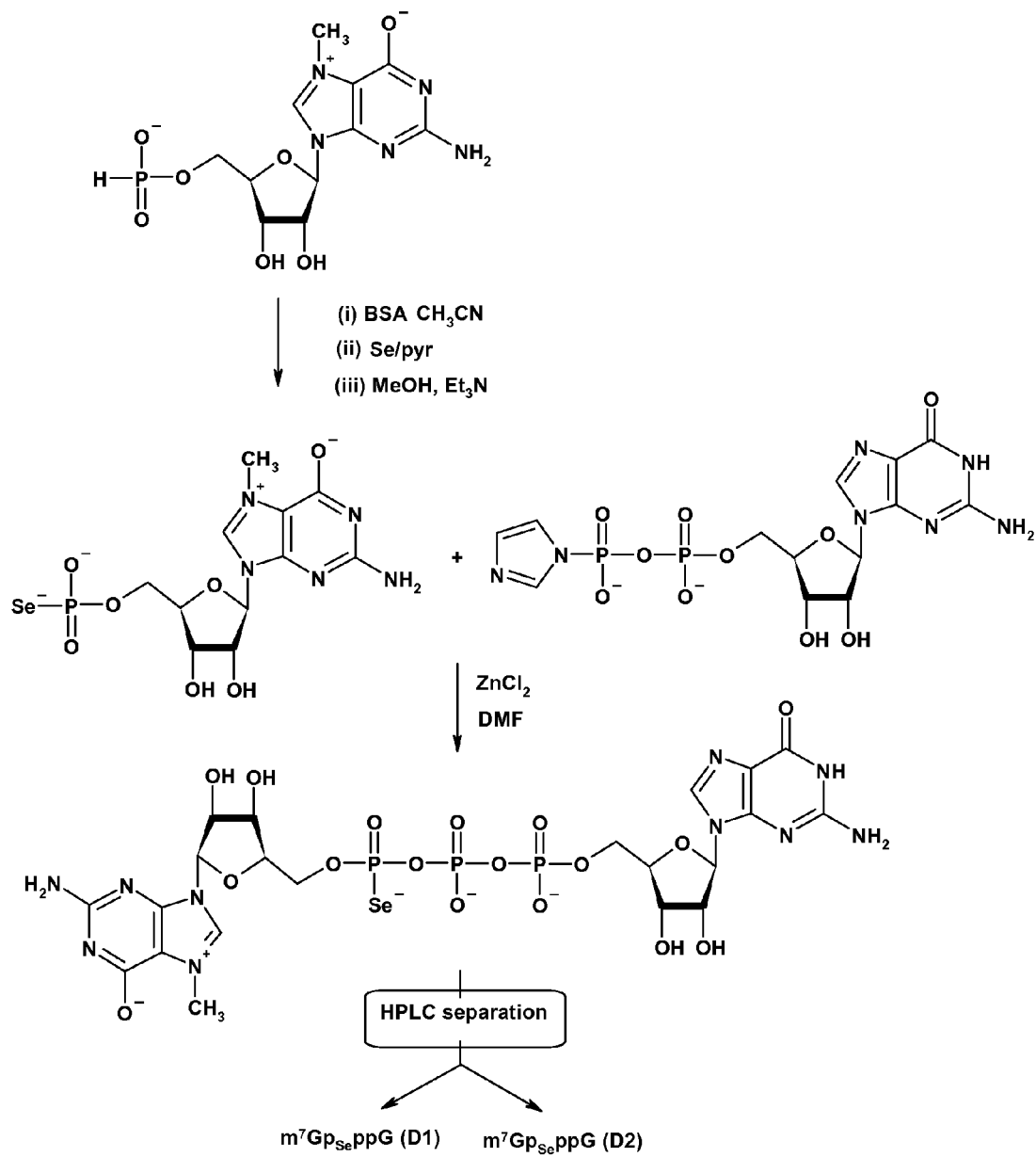
FIG. 6 depicts a synthesis of $m^7Gp_{Se}ppG$.
Figure 7:
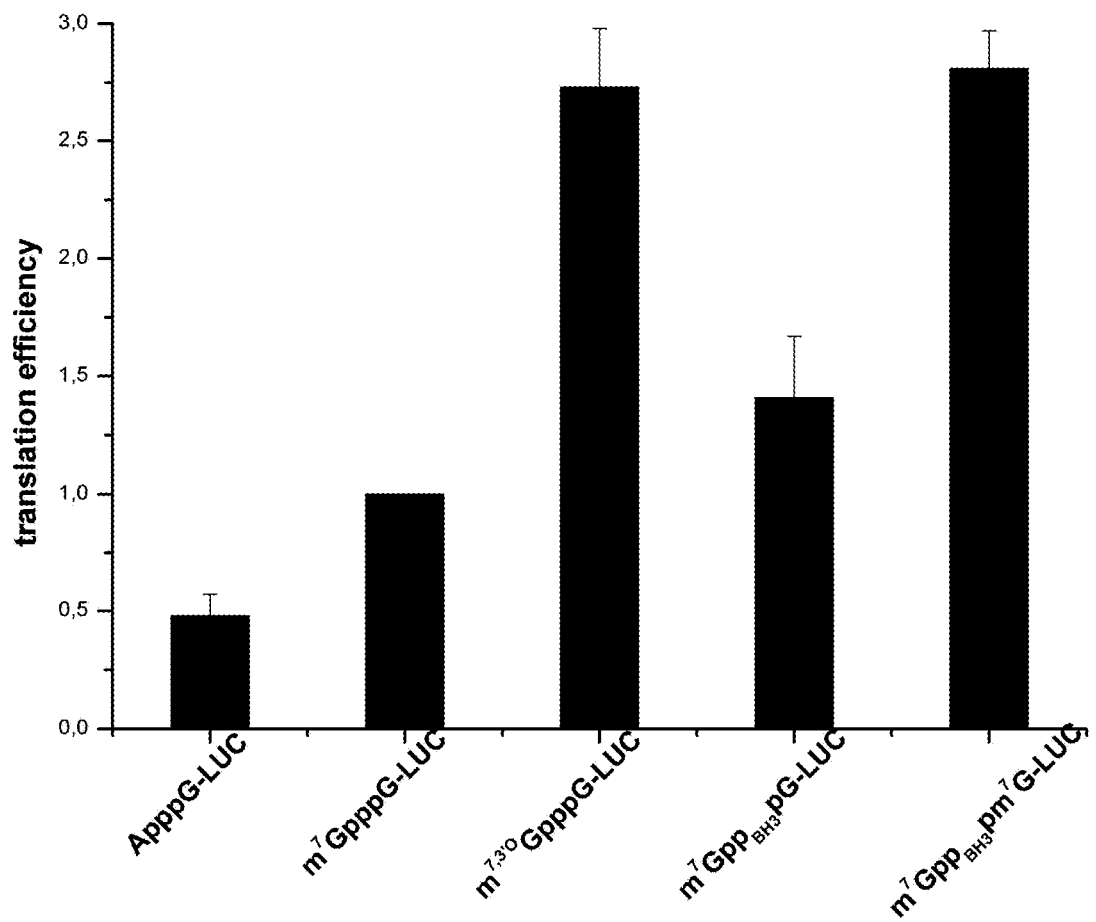
FIG. 7 depicts relative in vitro translational efficiencies of firefly luciferase mRNAs capped with ApppG (non-functional cap analog), $m^7$GpppG, $m_2^{7,3'-O}$GpppG, the boranophosphate cap analogs $m^7Gpp_{BH3}pG$ (diastereomeric 1:1 mixture), and $m^7Gpp_{BH3}pm^7G$.
Figure 8:
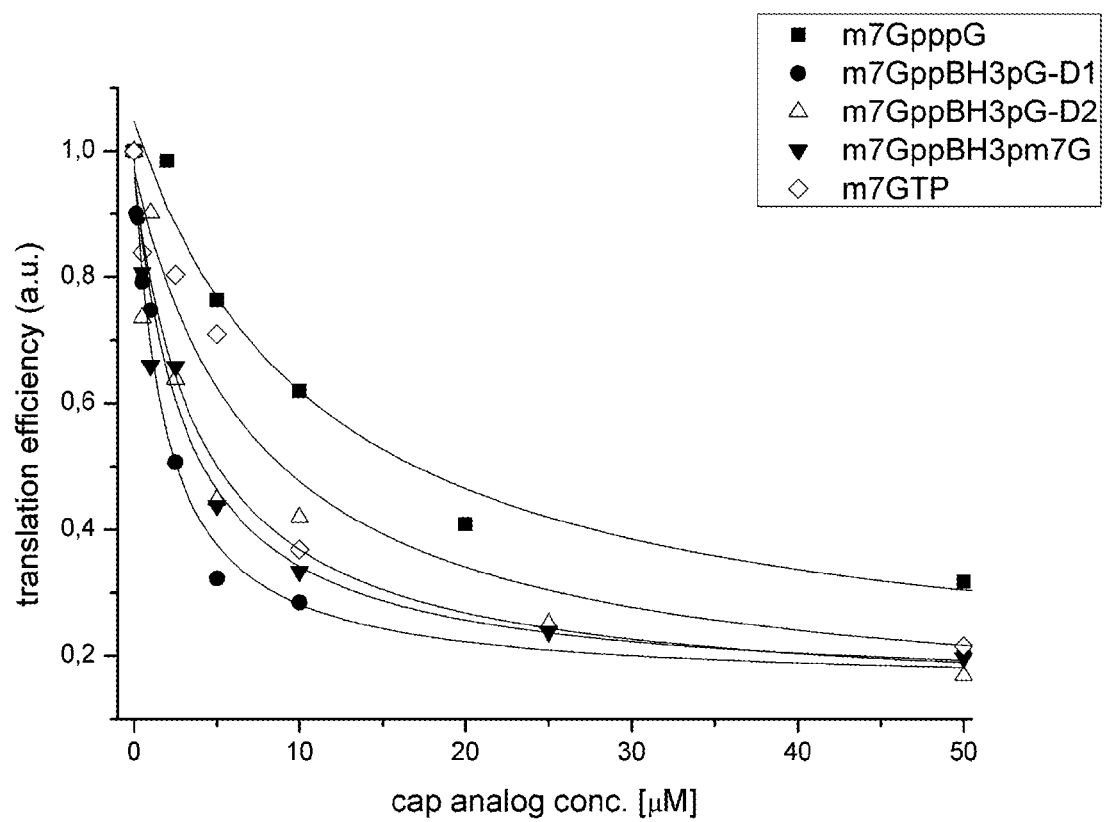
FIG. 8 depicts the inhibition of in vitro luciferase mRNA translation by boranophosphate cap analogs.
Figure 9:
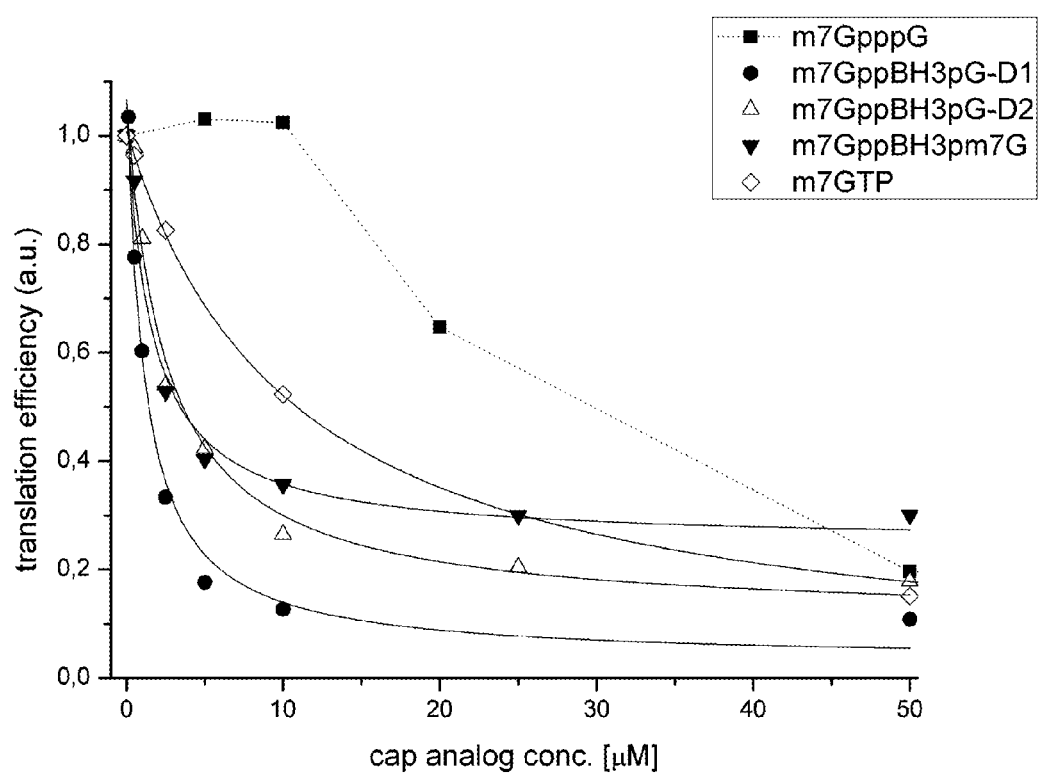
FIG. 9 depicts inhibition of in vitro luciferase mRNA translation by boranophosphate cap analogs incubated in rabbit reticulocyte lysate for 60 min before the start of translation.
Figure 10:
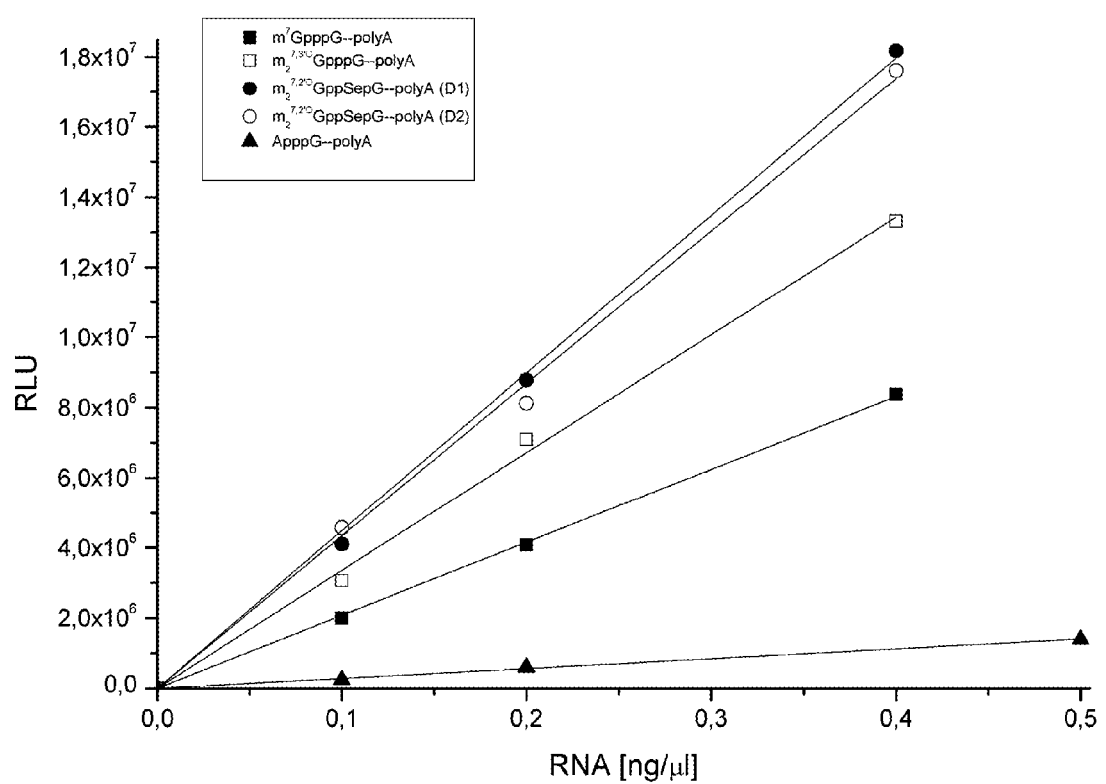
FIG. 10 depicts in vitro translational efficiencies of firefly luciferase mRNAs capped with ApppG, $m^7$GpppG, $m_2^{7,3'-O}$GpppG, and the phosphoroselenoate cap analogs $m_2^{7,2'-O}Gpp_{Se}pG$ (D1) and (D2).
Figure 11:
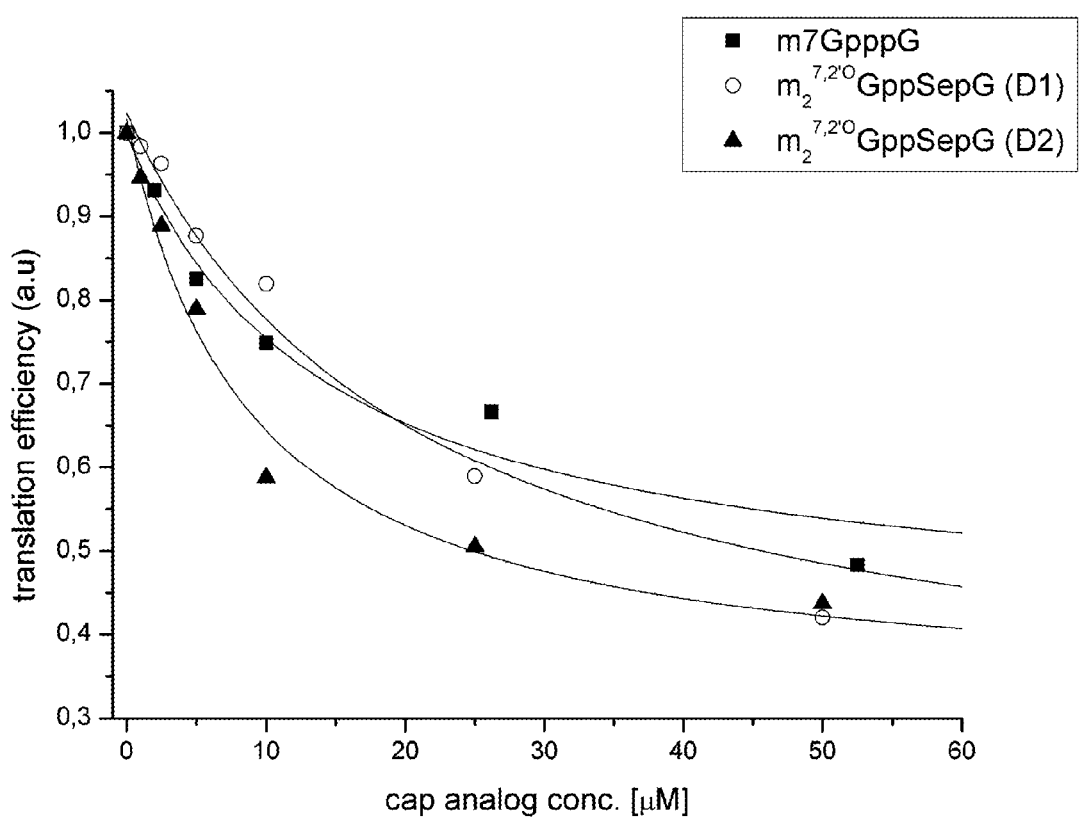
FIG. 11 depicts inhibition of in vitro luciferase mRNA translation by phosphoroselenoate cap analogs.
Figure 12:
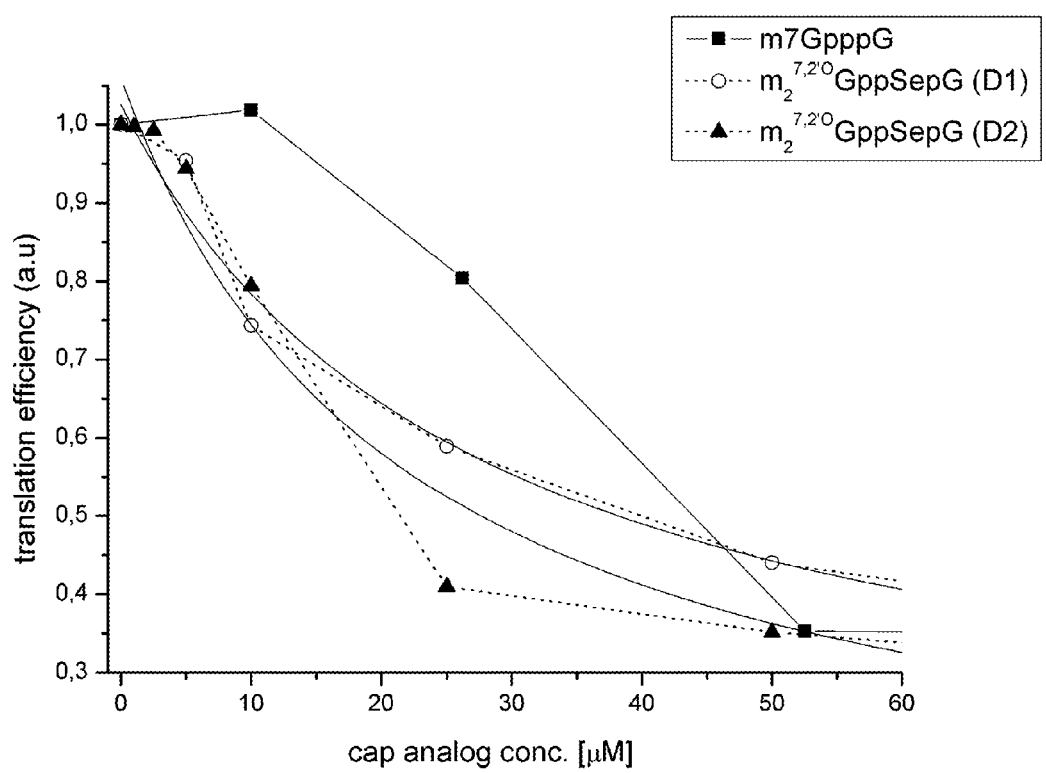
FIG. 12 depicts inhibition of in vitro luciferase mRNA translation by phosphoroselenoate cap analogs incubated in rabbit reticulocyte lysate for 60 min before the start of translation.
Figure 13:
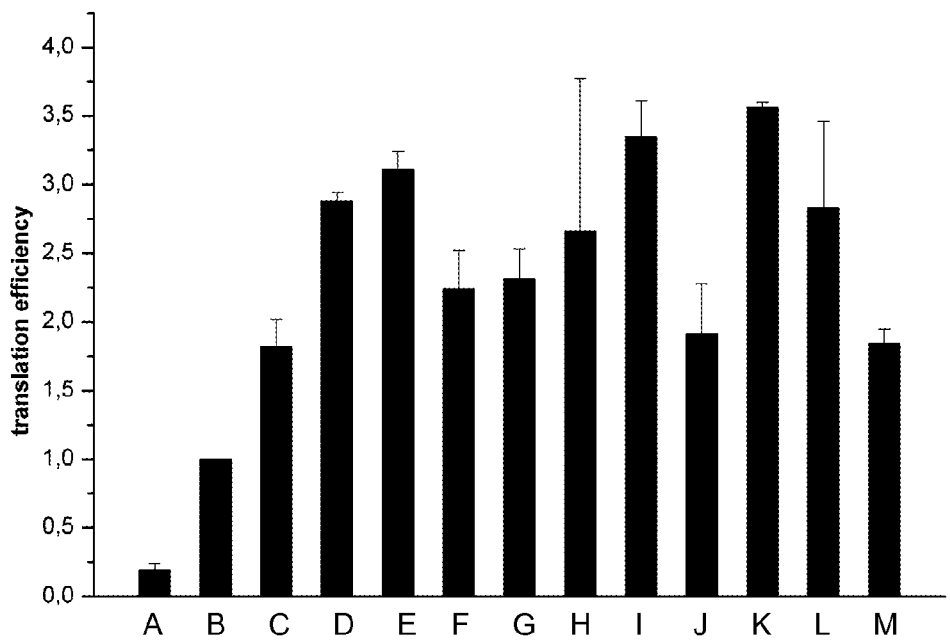
FIG. 13 depicts relative in vitro translational efficiencies of firefly luciferase mRNAs bearing $A_{31}$ poly-A tail, 5'-capped with various analogs.

FIG. 5 depicts the synthesis of $m_2^{7,2'-O}Gpp_{Se}pG$. The selenophosphate ($PSeO_3^{-3}$) was prepared by a modification of the method described in R. Glass et al., "Selenophosphate," *Meth. Enzymol.*, vol. 252, pp. 309-315 (1995). Trimethylsilyl phosphite was treated with selenium in pyridine to give trimethylsilyl selenophosphate, which was then desilylated by methanol in the presence of triethylamine to give the selenophosphate triethylammonium salt. This compound was coupled with the imidazolide derivative of 7,2'-O-dimethylguanosine 5'-monophosphate ($m_2^{7,2'-O}$GMP-Im) to give 7,2'-O-dimethylguanosine 5'-O-(2-selenodiphosphate) ($m_2^{7,2'-O}GDP\beta Se$). Anhydrous $ZnCl_2$ was used to mediate the coupling reaction; the $ZnCl_2$ dramatically increased the solubility of the reagents in DMF, and also accelerated the reaction rate. The reaction was very rapid; essentially 100% conversion of $m_2^{7,2'-O}$GMP-Im into $m_2^{7,2'-O}GDP\beta Se$ was observed by RP HPLC after 15 min. The $m_2^{7,2'-O}GDP\beta Se$ was unstable in acidic aqueous solutions (being hydrolyzed to $m_2^{7,2'-O}$GMP), and only moderately stable in neutral or basic solutions. Thus, care was taken to maintain the pH at 7 or above during purification of $m_2^{7,2'-O}GDP\beta Se$, which allowed the product to be isolated with 80% yield after ion-exchange chromatography. The $m_2^{7,2'-O}GDP\beta Se$ was then coupled with the imidazolide derivative of GMP in the presence of excess $ZnCl_2$. Two peaks were observed by RP HPLC, corresponding to two $m_2^{7,2'-O}Gpp_{Se}pG$ diastereomers, which were designated D1 and D2 according to their elution order. However, the coupling proceeded slowly, and complete disappearance of $m_2^{7,2'-O}GDP\beta Se$ took about two days. The extended reaction time allowed partial hydrolysis of $m_2^{7,2'-O}GDP\beta Se$ to $m_2^{7,2'-O}$GMP, and only a moderate reaction yield (40% conversion by HPLC, 25% isolated). The diastereomeric mixture of $m_2^{7,2'-O}Gpp_{Se}pG$ after isolation by ion-exchange chromatography was successfully resolved into pure diastereomers by RP HPLC. The products were characterized by mass spectrometry, $^1$H NMR, and $^{31}$P NMR to confirm structures and homogeneity. The D1 and D2 isomers of $m_2^{7,2'-O}Gpp_{Se}pG$ were stable in aqueous solution, did not undergo appreciable hydrolysis or oxidation, and could be stored as solids, protected from moisture at −20° C., for at least three months.

Other $BH_3$- and Se-analogs have also been and will also be produced by reactions generally analogous to those depicted in FIGS. 1-6.

Example 1

General Procedures for Isolation and Characterization of Cap Analogs

Intermediate nucleotides were separated by ion-exchange chromatography on a DEAE-Sephadex A-25 column ($HCO_3^-$ form) with a linear gradient of triethylammonium bicarbonate (TEAB) in deionized water. After evaporation under reduced pressure with addition of ethanol, the intermediates were isolated as triethylammonium salts. Final products (the cap analogs) were further separated by semi-preparative RP HPLC and, after repeated freeze-drying, were isolated as ammonium salts. Analytical HPLC was performed on an Agilent Technologies 1200 Series apparatus, using a Supelcosil LC-18-T RP column (4.6×250 mm, flow rate 1.3 ml/min) with a linear gradient of 0%-25% methanol in 0.05 M ammonium acetate buffer (pH 5.9). Eluting compounds were detected with a UV-Vis detector (at 260 nm), and a fluorescence detector (excitation at 280 nm and emission at 337 nm). Semipreparative HPLC was performed on a Waters 600E Multisolvent Delivery System apparatus and a Waters Discovery RP Amide C16 reverse phase column (21.2 mm×250 mm, flow rate 5.0 ml/min) with a linear gradient of methanol in 0.05 M ammonium acetate buffer (pH 5.9), and UV detection at 260 nm. $^1$H NMR and $^{31}$P NMR spectra were recorded at 25° C. on a Varian UNITY-plus spectrometer at 399.94 MHz and 161.90 MHz, respectively. $^1$H NMR chemical shifts were determined relative to sodium 3-trimethylsilyl-[2,2,3,3-

D4]-propionate (TSP) in $D_2O$ as an internal standard. $^{31}P$ NMR chemical shifts were determined relative to 20% phosphorus acid in $D_2O$ as an external standard. Mass spectra in electrospray negative ion mode [(ESI MS (−))] were recorded on a Micromass QToF 1 MS spectrometer. Solvents and other reagents were purchased from Sigma-Aldrich, and were used without further treatment unless otherwise stated. Acetonitrile and acetone were distilled over $P_2O_5$ and stored over 4 Å molecular sieves before use. GMP and GDP were converted into triethylammonium salts with a Dowex 50 WX8 ion-exchange resin. $m_2^{7,2'-O}GMP$ and $m_2^{7,2'-O}GDP$ were prepared as previously reported by J. Jemielity et al. (2003).

Example 2

General Procedure for Synthesis of Nucleotide Imidazolide Derivatives

GMP-Im, $m_2^{7,2'-O}GMP$-Im, GDP-Im, and $m_2^{7,2'-O}GDP$-Im were prepared as described by T. Mukaiyama et al., "Phosphorylation by oxidation-reduction condensation. Preparation of active phosphorylating reagents," *M. Bull. Chem. Soc. Jpn.*, vol. 44, p. 2284 (1971). The nucleotide (1 equiv., TEA salt), imidazole (8 equiv.), and 2,2'-dithiodipyridine (3 equiv.) were mixed in DMF (~2.5 ml/100 mg of nucleotide). Triethylamine (2 equiv.) and triphenylphosphine (3 equiv.) were added, and the mixture was stirred for 6-8 h. The product was precipitated from the reaction mixture with a solution of anhydrous $NaClO_4$ (1 equiv. per negative charge) in dry acetone (~8 ml per ml of DMF). After cooling at 4° C., the precipitate was filtered, washed repeatedly with cold, dry acetone, and dried in vacuum over $P_4O_{10}$. Yields were 80%-100%.

Example 3

Guanosine 5'-(H-phosphonate)

This preparation followed that of M. Yoshikawa et al., "Studies of phosphorylation. IV. The phosphorylation of nucleosides with phosphorus trihalide," *Bull. Chem. Soc. Jpn.*, vol. 43, pp. 456-461 (1970). 2',3'-O,O-isopropylidene guanosine (1.3 g, 4.0 mmol) was suspended in 19.5 ml of trimethylphosphate and cooled to 0° C. on ice. $PCl_3$ (1.06 ml, 12.1 mmol) was added, and the mixture was stirred at 0° C. for 1 h. The reaction mixture was diluted with water (80 ml), adjusted to pH ~1.5 with solid $NaHCO_3$ and heated to 70° C. for 1 h. The solution was allowed to cool to room temperature, adjusted to pH ~6 with $NaHCO_3$, diluted with 80 ml of water, and subjected to chromatography on DEAE Sephadex with a 0-0.9 M gradient of TEAB. Fractions eluting at 0.6-0.65 M TEAB and containing ~3.0 mmol of product were collected, evaporated, and dried in a vacuum dessicator over $P_2O_5$. This produced 1.34 g of guanosine 5'-(H-phosphonate) triethylammonium salt (yield 75%). ESI MS (−) m/z: 346.08 (calc. for $C_{10}H_{13}N_5O_7P$: 346.06). $^1H$ NMR δ (ppm): 8.08 (1H, s, H8); 6.73 (1H, d, J=640 Hz, H—P); 5.93 (1H, d, J=~5.4 Hz, H1'); 4.77 (1H, t, J=~5.4 Hz); 4.48 (1H, t, J=3.2 Hz); 4.32 (1H, m, H4'); 4.11 (2H, m, H5' and H5"). $^{31}P$ NMR δ (ppm): 7.07 (1P, dt, J=640 Hz, J=6.0 Hz).

Example 4

Guanosine 5'-O-boranophosphate, Triethylammonium Salt

Guanosine 5'-(H-phosphonate) (1.03 g, 2.3 mmol) was placed in a round-bottom flask and suspended in 30 ml of dry acetonitrile. The flask was sealed with a rubber septum and flushed with argon for 30 min. N,O-bistrimethylsilylacetamide (11.3 ml, 46 mmol) was injected through a syringe, and the mixture was vigorously stirred until a clear solution was obtained, and was then stirred for an additional 30 min. The solution was then cooled in an ice bath, and a 2 M solution of $BH_3 \cdot SMe_2$ complex in THF (5.7 ml, 11.5 mmol) was added. After 5 min, the flask was removed from the ice bath, and stirring continued for 30 min. The solution was evaporated under reduced pressure to an oily residue, placed again in an ice bath, treated with 60 ml of methanol and 3 ml of 2 M ammonia in ethanol, and then stirred for 2 h at RT. The solution was evaporated under reduced pressure to dryness, dissolved in 100 ml of water, and extracted once with 20 ml diethyl ether. The ether was removed from the aqueous layer under reduced pressure. The products were separated on DEAE Sephadex with a 0-0.9 M gradient of TEAB. Fractions containing 13,200 optical density units of product were evaporated to dryness, dissolved in water, and freeze-dried to yield 410 mg of guanosine 5'-O-boranophosphate triethylammonium salt (32%). ESI MS (−) m/z: 360.13 (calc for $C_{10}H_{16}N_5O_7P^{11}B$: 360.09). $^1H$ NMR δ (ppm): 8.17 (1H, s, H8); 5.82 (1H, d, J=6.0 Hz, H1'); 4.74 (1H, t, H2'); 4.47 (1H, t, H3'); 4.32 (1H, m, H4'), 4.03 (2H, m, H5' and H5"). $^{31}P$ NMR δ (ppm): 79.05 (1P, ~qq, J=158 Hz, J=22.5 Hz).

Example 5

Synthesis of $m^7Gppp_{BH3}G$

To a mixture of $GMPBH_3$ (50 mg, 0.089 mmol, TEA salt) and $m^7GDP$-Im (100 mg, 0.18 mmol, sodium salt) in 2.5 ml of $DMF/H_2O$ (9:1) was added anhydrous $MgCl_2$ (110 mg, 1.16 mmol) portionwise, and the mixture was vigorously shaken until all reagents were dissolved. The solution was stirred at RT for 3 days, and then the reaction was quenched by addition of EDTA (430 mg, 1.16 mmol) in 25 ml of water with pH adjusted to ~6 by addition of solid $NaHCO_3$. Products were separated on DEAE Sephadex with a 0-1.2 M gradient of TEAB. A diastereomeric mixture of $m^7Gppp_{BH3}G$ was obtained (685 optical density units). Diastereomers were resolved by semi-preparative HPLC and freeze-dried three times. The yield after HPLC separation was 13.4 mg of $m^7Gppp_{BH3}G$ (D1) and 7.3 mg of $m^7Gppp_{BH3}G$ (D2) (18% and 9.8%, respectively). ESI MS (−) m/z: 799.22 (calc. for $C_{21}H_{31}N_{10}O_{17}P_3B$: 799.12). D1: $^1H$ NMR δ (ppm): 8.93 (1H, s. H8 $m^7G$); 7.99 (1H, s, H8 G); 5.79 (1H, d, J=3.2 Hz, H1' $m^7G$); 5.73 (1H, d, J=6.0 Hz, H1' G); 4.59 (1H, ~t, H2' G); 4.48 (1H, dd, J=4.4 Hz, J=3.2 Hz, H2' $m^7G$); 4.40 (1H, m, H3; G); 4.37 (1H, m, H3' $m^7G$); 4.27 (3H, overlapped m, H4', H5', H5"); 4.13 (3H, overlapped m, H4', H5', H5"); 3.95 (3H, s, $CH_3$); 0.34 (3H, broad m, $BH_3$). $^{31}P$ NMR δ (ppm): 84.07 (1P, m, Pα ($P_{BH3}$)); −11.29 (1P, d, J=19.4 Hz, Pγ); −22.95 (1P, dd, J=19.4 Hz, J=30.0 Hz, $P_β$). D2: $^1H$ NMR δ (ppm): 8.87 (1H, s. H8 $m^7G$); 7.95 (1H, s, H8 G); 5.79 (1H, d, J=~2 Hz, H1' $m^7G$); 5.68 (1H, d, J=5.4 Hz, H1' G); 4.62 (1H, ~t, H2' G); 4.50 (1H, ~t, H2' $m^7G$); 4.41 (1H, m, H3' G); 4.37 (1H, m, H3' $m^7G$); 4.25 (3H, overlapped m, H4', H5', H5"); 4.15 (3H, overlapped m, H4', H5', H5"); 3.93 (3H, s, $CH_3$); 0.34 (3H, broad m, $BH_3$). $^{31}P$ NMR δ (ppm): 84.0 (1P, m, Pβ ($P_{BH3}$)); −11.38 (1P, s, Pγ); −22.88 (1P, s, $P_β$).

Example 6

$m_2^{7,2'-O}Gpp_{BH3}G$

To a mixture of $GMPBH_3$ (30 mg, 0.053 mmol, TEA salt) and $m_2^{7,2'-O}GDP$-Im (60 mg, 0.11 mmol, sodium salt) in 1.5 ml of DMF/H$_2$O (9:1) was added anhydrous MgCl$_2$ (80 mg, 0.85 mmol) portionwise, and the mixture was vigorously shaken until all reagents were dissolved. The solution was stirred at room temperature for 4 days, and then the reaction was quenched by addition of EDTA (320 mg, 0.85 mmol) in 25 ml water with pH adjusted to ~6 by addition of solid NaHCO$_3$. Products were separated on DEAE Sephadex with a 0-1.2 M gradient of TEAB. A diastereomeric mixture of m$_2^{7,2'-O}$Gpp$_{BH3}$G was obtained (520 optical density units). The diastereomers were resolved by semi-preparative HPLC and freeze-dried three times. The yield after HPLC separation was 6.1 mg of m$_2^{7,2'-O}$Gppp$_{BH3}$G (D1) and 3.7 mg of m$_2^{7,2'-O}$Gppp$_{BH3}$G (D2) (13.4% and 8.0%, respectively). ESI MS (−) m/z: 813.15 (calc. for C$_{22}$H$_{33}$N$_{10}$O$_{17}$P$_3$$^{11}$B: 813.13). D1: $^1$H NMR δ (ppm): 9.03 (1H, s, H8 m$^7$G); 8.09 (1H, s, H8G); 5.95 (1H, d, J=2.7 Hz, H1' m$^7$G); 5.84 (1H, d, J=6.0 Hz, H1' G); 4.70 (1H, dd, J=6.0 Hz, J=5.1 Hz, H2' G); 4.56 (1H, ~t, H3' m$^7$G); 4.50 (1H, dd, J=3.5 Hz, 5.1 Hz, H3' G); 4.41 (1H, m, H5' G); 4.34 (2H, m, overlapped H4' m$^7$G, H4'G); 4.27 (2H, m overlapped, H2' m$^7$G, H5"G); 4.24 (2H, m, H5', H5" m$^7$G); 4.08 (3H, s, N—CH$_3$); 3.60 (3H, s, O—CH$_3$), 0.40 (3H, m, BH$_3$). $^{31}$P NMR δ (ppm): 83.7 (1P, m, Pβ (P$_{BH3}$)), −11.30 (1P, d, J=19.5 Hz, Pγ); −22.91 (1P, dd, J=19.5 Hz, J=30.0 Hz, P$_α$). D2: $^1$H NMR δ (ppm): 8.98 (1H, s, H8 m$^7$G); 8.06 (1H, s, H8G); 5.96 (1H, d, J=2.7 Hz, m$^7$G); 5.79 (1H, d, J=5.9 Hz, H1' G); 4.61 (1H, ~t, H2' G); 4.50 (1H, ~t, H3' m$^7$G); 4.45 (1H, dd, J=3.5 Hz, 5.1 Hz, H3' G); 4.34 (2H, m (overlapped), H4' m$^7$G, H5' G); 4.26 (3H, m (overlapped), H2' m$^7$G, H4' G, H5"G); 4.20 (2H, m, H5', H5" m$^7$G); 4.06 (3H, s, N—CH$_3$); 3.61 (3H, s, O—CH$_3$), 0.40 (3H, m, BH$_3$). $^{31}$P NMR δ (ppm): 83.7 (1P, m, Pα (P$_{BH3}$)), −11.41 (1P, d, J=19.0 Hz, Pγ); −22.87 (1P, dd, J=19.0 Hz, J=32.0 Hz P$_β$).

Example 7

Boranophosphate Triethylammonium Salt

This salt was prepared by a modification of the procedure of V. Nahum et al., "Boranophosphate Salts as an Excellent Mimic of Phosphate Salts: Preparation, Characterization, and Properties," *J. Inorg. Chem.* vol. 20, pp. 4124-4131 (2004). Tris(trimethylsilyl)phosphite (600 μl, 1.8 mmol) was added to a round-bottom flask containing 5 ml dry acetonitrile. The flask was sealed with a rubber septum and flushed with argon for 30 min. N,O-bistrimethylsilylacetamide (1.5 ml, 5.4 mmol) was injected through a syringe. After 30 min., the solution was cooled in an ice-bath, and a 2 M solution of BH$_3$.SMe$_2$ complex in THF (1.35 ml) was added. After 5 min, the flask was removed from the ice bath, and stirring continued for 30 min. The solution was then evaporated under reduced pressure to an oily residue, placed again in the ice bath, treated with 20 ml of methanol and 0.5 ml of triethylamine, and was then stirred for 2 h at room temperature. The solution was evaporated to dryness, and the residue was dried over P$_2$O$_5$. The yield of [HN(CH$_2$CH$_3$)$_3$]$_2$HPO$_3$BH$_3$ was 530 mg (17.8 mmol) (97%, contaminated with acetamide). This boranophosphate triethylammonium salt was stored at 4° C., and was used for further reactions in this form. $^1$H NMR δ (ppm): 0.33 (~dq, J$_{B—H}$=87.8 Hz, J$_{P—H}$=22.3 Hz). $^{31}$P NMR δ (ppm): 84.3 (~qq, J$_{P—B}$=147 Hz, J$_{P—H}$=22.3 Hz).

Example 8

Gpp$_{BH3}$pG

The imidazolide derivative of GMP (GMP-Im) (200 mg, 0.46 mmol, sodium salt) and the previously obtained boranophosphate triethylammonium salt (70 mg, 0.23 mmol) were suspended in 4 ml of DMF, and anhydrous MgCl$_2$ (380 mg, 4 mmol) was added portionwise. After 1 h the reaction was quenched by addition of EDTA (1.48 mg, 4 mmol) in 40 ml of water, and the pH was adjusted to ~6 by addition of solid NaHCO$_3$. The product was separated on DEAE Sephadex with a 0-1.2 M gradient of TEAB. After evaporation 165 mg (4,000 optical density units at 260 nm) of Gpp$_{BH3}$pG triethylammonium salt were obtained (65% yield). ESI MS (−) m/z: 785.12 (calc for. C$_{20}$H$_{29}$N$_{10}$O$_{17}$P$_3$B: 785.10). $^1$H NMR δ (ppm): 8.11 (1H, s, H8 G$^{A*}$); 8.09 (1H, s, H8 G$^B$); 5.84 (2H, d, J=5.2 Hz, H1' G$^{AB}$); 4.69 (2H, ~t, J=5.1 Hz, H1' G$^{AB}$); 4.50 (1H, ~t, H3' G$^{AorB}$); 4.49 (1H, ~t, H3' G$^{AorB}$); 4.31 (2H, m, H4' G$^{AB}$); 4.24 (4H, m, H5' G$^{AB}$, H5" G$^{AB}$). $^{31}$P NMR δ (ppm): 75.10 (1P, m, P$_β$ (P$_{BH3}$)), −11.20 (1P$^{A*}$, ~dt, J=30.2 Hz, J=~5 Hz), −11.28 (1P$^{B*}$, ~dt, J=30.2 Hz, J=~5 Hz). *A and B denote signals from diastereotopic nuclei.

Example 9 m$^7$Gpp$_{BH3}$pG

Gpp$_{BH3}$pG (35 mg, TEA salt) was dissolved in 1.5 ml of DMSO, and 20 μl of methyl iodide were added. After 4 h, the reaction was quenched by addition of 15 ml water, and the pH was adjusted to ~7 with solid NaHCO$_3$. Products were separated on DEAE Sephadex with a 0-1.2 M gradient of TEAB. A diastereomeric mixture of m$^7$Gpp$_{BH3}$pG (550 optical density units) was collected and the solvent was evaporated. The product was then dissolved in a small amount of water and converted to the sodium salt on Dowex resin. Diastereomers were subsequently resolved by semi-preparative HPLC, and freeze-dried three times. Yields after HPLC separation were 10.2 mg of m$^7$Gpp$_{BH3}$pG (D1) and 9.8 mg of m$^7$Gpp$_{BH3}$pG (D2) as NH$_4^+$ salts (37.2% and 35.6%, respectively). ESI MS (−) m/z: 799.13 (calc. for C$_{21}$H$_{31}$N$_{10}$O$_{17}$P$_3$B: 799.12). D1: $^1$H NMR δ (ppm): 8.02 (1H, s, H8G); 5.89 (1H, d, J=3.0 Hz, H8 m$^7$G); 5.80 (1H, d, J=6.2 Hz, H8G); 4.68 (1H, ~t, H2' G); 4.51 (1H, ~t, H2' m$^7$G); 4.50 (1H, ~t, H3' G); 4.42 (1H, ~t, H3' G); 4.35 (3H, m (overlapped), H4', H5', H5" G); 4.22 (3H, m (overlapped), H4', H5', H5" m$^7$G), 4.06 (3H, s, CH$_3$), 0.53 (3H, m, BH$_3$). $^{31}$P NMR δ (ppm): 75.1 (1P, m, P$_β$ (P$_{BH3}$)), −11.3 (2P, ~d, J$_{Pα-Pβ}$=30.7 Hz, P$_α$ and Pγ). D2: $^1$H NMR δ (ppm): 8.04 (1H, s, H8G); 5.92 (1H, d, J=3.0 Hz, H8 m$^7$G); 5.82 (1H, d, J=6.2 Hz, H8G); 4.68 (1H, ~t, H2' G); 4.51 (1H, ~t, H2' m$^7$G); 4.50 (1H, ~t, H3' G); 4.42 (1H, ~t, H3' G); 4.35 (3H, m (overlapped), H4', H5', H5" G); 4.22 (3H, m (overlapped), H4', H5', H5" m$^7$G), 4.06 (3H, s, CH$_3$); 0.53 (3H, m, BH$_3$). $^{31}$P NMR δ (ppm): 75.13 (1P, m, P$_β$ (P$_{BH3}$)), −11.31 (2P, ~d, J$_{Pα-Pβ}$=30.7 Hz, Pγ and P$_α$).

Example 10 m$^7$Gpp$_{BH3}$pm$^7$G (Method I)

Gpp$_{BH3}$pG (50 mg, 800 optical density units, TEA salt) was dissolved in 1.0 ml of DMSO, and 30 μl of methyl iodide were added. After 2 h, an additional 30 μl of methyl iodide were added. After 2 h, the reaction was quenched by adding 15 ml water and adjusted to pH ~7 with solid NaHCO$_3$. Products were separated on DEAE Sephadex with a 0-1.2 M gradient of TEAB. m$^7$Gpp$_{BH3}$pm$^7$G (200 optical units density) was collected, evaporated, and converted into the sodium salt on Dowex resin. Finally, the product was precipitated with ethanol and dried over P$_2$O$_5$. The yield was 22 mg of m$^7$Gpp$_{BH3}$pm$^7$G (sodium salt) (54%). ESI MS (−) m/z: 813.10 (calc for. C$_{22}$H$_{33}$N$_{10}$O$_{17}$P$_3$$^{11}$B: 813.13). $^1$H NMR δ

(ppm): 9.02 (2H, s, H8 m$^7$G); 6.04 (2H, d, J=3.7 Hz, H2' G); 4.67 (2H, ~t, H2' m$^7$G); 4.53 (2H, ~t, H3' m$^7$G); 4.40 (2H, m, H4' m$^7$G); 4.36 (2H, m, H5' m$^7$G); 4.23 (2H, m, H5'' m$^7$G); 4.13 (6H, s, CH$_3$); 0.44 (3H, m, BH$_3$). $^{31}$P NMR δ (ppm): 74.90 (1P, m, P$_β$ (P$_{BH3}$)), −11.33 (1P$^{A*}$, ~d, J$_{Pα-Pβ}$=31.0 Hz), −11.36 (1P$^{B*}$, ~d, J$_{Pα-Pβ}$=31.0 Hz). *A and B denote diastereotopic nuclei.

Example 11 m$^7$Gpp$_{BH3}$pm$^7$G (Method II)

The imidazolide derivative of m$^7$GMP (m$^7$GMP-Im) (225 mg, 0.5 mmol, sodium salt) and boranophosphate triethylammonium salt (75 mg, 0.25 mmol, sodium salt) were suspended in 4 ml of DMF, and anhydrous MgCl$_2$ (380 mg, 4 mmol) was added portionwise. After 1 h the reaction was quenched by adding EDTA (1.48 mg, 4 mmol) in 40 ml of water, and the pH was adjusted to ~6 by addition of solid NaHCO$_3$. The product was separated on DEAE Sephadex with a 0-1.1 M gradient of TEAB. After evaporation of solvent, the product was dissolved in a small amount of water and converted into the sodium salt on Dowex resin. After precipitation with ethanol and drying over P$_2$O$_5$, 150 mg of m$^7$Gpp$_{BH3}$pm$^7$G sodium salt were obtained (34% yield). (Spectral data are given under the description of Method I above.)

Example 12 m$_2^{7,2'-O}$Gpp$_{BH3}$pG

To a suspension of m$_2^{7,2'-O}$GMP-Im (15 mg, 0.03 mmol, sodium salt) and boranophosphate triethylammonium salt (30 mg, 0.1 mmol) in 0.5 ml of DMF, anhydrous MgCl$_2$ (40 mg, 0.4 mmol) was added portionwise, and the mixture was shaken until reagents dissolved (1-2 min). Then GMP-Im (40 mg, 0.09 mmol) and MgCl$_2$ (40 mg) were added to the reaction mixture. The reaction was quenched after 5 h by addition of EDTA (0.8 mmol) in 10 ml of water, and the pH was adjusted to ~6 with solid NaHCO$_3$. Products were separated by semi-preparative HPLC and freeze-dried three times. Yields were 5.1 mg of m$_2^{7,2'-O}$Gpp$_{BH3}$pG (D1) and 4.8 mg of m$_2^{7,2'-O}$Gpp$_{BH3}$pG (D2) as NH$_4^+$ salts (18% and 17%, respectively). ESI MS (−) m/z: 813.14 (calc. for C$_{22}$H$_{33}$N$_{10}$O$_{17}$P$_3^{11}$B: 813.13). D1: $^1$H NMR δ (ppm): 9.04 (1H, s, H8 m$^7$G); 8.10 (1H, s, H8G); 5.97 (1H, d, J=2.9 Hz, H1' m$^7$G); 5.80 (1H, d, J=5.9 Hz, H1' G); 4.70 (1H, ~t, H2' G); 4.56 (1H, ~t, H3' m$^7$G); 4.50 (1H, ~t Hz, H3' G); 4.41 (1H, m, H5' G); 4.34 (2H, m, overlapped H4' m$^7$G, H4'G); 4.27 (2H, m overlapped, H2' m$^7$G, H5''G); 4.24 (2H, m, H5', H5'' m$^7$G); 4.08 (3H, s, N—CH$_3$); 3.59 (3H, s, O—CH$_3$), 0.45 (3H, m, BH$_3$). $^{31}$P NMR δ (ppm): 75.12 (1P, m, P$_β$ (P$_{BH3}$)), −11.09 (2P, ~d, J$_{Pα-Pβ}$=30.7 Hz, P$_α$ and P$_γ$). D2: $^1$H NMR δ (ppm): 9.00 (1H, s, H8 m$^7$G); 8.08 (1H, s, H8G); 5.96 (1H, d, J=2.9 Hz, H1' m$^7$G); 5.81 (1H, d, J=5.9 Hz, H1' G); 4.70 (1H, ~t, H2' G); 4.55 (1H, ~t, H3' m$^7$G); 4.48 (1H, ~t, H3' G); 4.40 (2H, m (overlapped), H4' m$^7$G, H5' G); 4.30 (3H, m (overlapped), H2' m$^7$G, H4' G, H5''G); 4.25 (2H, m, H5', H5'' m$^7$G); 4.07 (3H, s, N—CH$_3$); 3.62 (3H, s, O—CH$_3$), 0.45 (3H, m, BH$_3$). $^{31}$P NMR δ (ppm): 75.12 (1P, m, P$_β$ (P$_{BH3}$)), −11.11 (2P, ~d, J$_{Pα-Pβ}$=30.7 Hz, P$_α$ and P$_γ$).

Example 13

Selenophosphate Triethylammonium Salt

A suspension of selenium (160 mg, 2 mmol) in pyridine (1 ml) was added dropwise through a syringe into a septum-sealed and argon-bubbled solution of tris(trimethylsilyl) phosphite (600 μl, 1.8 mmol) in dry CH$_3$CN (20 ml). The resulting solution was held at room temperature for 30 min, and was then evaporated to dryness. Then a solution of triethylamine (500 μl, 3.6 mmol) in MeOH (20 ml) was added, and the mixture was stirred at room temperature for 2 h. The solvent was removed under reduced pressure and the residue re-evaporated twice with methanol. The product, which was obtained as an oily, yellowish residue, was used without further treatment in the following reaction:

Example 14

7,2'-O-dimethylguanosine 5'4)-(2-selenodiphosphate) (m$_2^{7,2'-O}$GDPβSe)

To a suspension of 7,2'-O-dimethylguanosine 5'-O-phosphate imidazolide (250 mg, 0.43 mmol) and selenophosphate triethylammonium salt (prepared from 600 μl of (Me$_3$SiO)$_3$P) in 5 ml of DMF, was added anhydrous ZnCl$_2$ (590 mg, 4.30 mmol) and the mixture was vigorously shaken until all reagents dissolved (3 min). The resulting solution was stirred for 20 min at room temperature, and the reaction was then quenched by adding a solution of disodium EDTA (1.6 g, 4.30 mmol) and 800 mg of NaHCO$_3$ in 300 ml of water. The pH was adjusted to ~7 with solid NaHCO$_3$ as necessary. The product was isolated on DEAE Sephadex with a 0-1.0 M gradient of TEAB. The yield was 254 mg (0.35 mmol) of m$_2^{7,2'-O}$GDPβSe as the TEA salt (81%). ESI MS (−) m/z: 553.85 (calc. for C$_{12}$H$_{18}$N$_5$O$_{10}$P$_2^{80}$Se: 533.97).

Example 15 m$_2^{7,2'-O}$Gpp$_{Se}$pG m$_2^{7,2'-O}$GDPβSe (250 mg, 0.35 mmol) and GMP-Im (250 mg, 0.50 mmol) were suspended in 5 ml of DMF, and anhydrous ZnCl$_2$ (480 mg, 3.5 mmol) was added. The resulting solution was kept at room temperature for 2 days. The reaction was quenched by adding disodium EDTA (1.3 g, 3.5 mmol) in 100 ml of water, and neutralized with solid NaHCO$_3$. Products were isolated on DEAE Sephadex with a 0-1.2 M gradient of TEAB. Finally, the diastereomers were separated by semi-preparative HPLC and freeze-dried three times. Yields were 40 mg (0.045 mmol) of m$_2^{7,2'-O}$Gpp$_{Se}$pG (D1) and 35 mg (0.040 mmol) of m$_2^{7,2'-O}$Gpp$_{Se}$pG (D2) as NH$_4^+$ salts (13% and 11%, respectively). ESI MS (−) m/z: 878.99 (calc. for C$_{22}$H$_{30}$N$_{10}$O$_{17}$P$_3^{80}$Se: 879.02). D1: $^1$H NMR δ (ppm): 9.02 (1H, s, H8 m$^7$G); 8.04 (1H, s, H8G); 5.97 (1H, d, J=2.4 Hz, H1' m$^7$G); 5.81 (1H, d, J=6.3 Hz, H1' G); 4.69 (1H, ~t, H2' G); 4.55 (1H, ~t, H3' m$^7$G); 4.54 (1H, ~t, H3' G); 4.43 (1H, m, H5' G); 4.32 (2H, overlapped m, H4'G, H5''G); 4.26 (4H, m overlapped, H2' m$^7$G, H4' m$^7$G, H5' m$^7$G, H5'' m$^7$G); 4.06 (3H, s, N—CH$_3$); 3.59 (3H, s, O—CH$_3$). $^{31}$P NMR δ (ppm): 17.4 (1P, ~t, J=29.6 Hz, P$_β$ ($P_{BH3}$)), −12.4 (2P, ~d, J=29.6 Hz, $P_\alpha$ and $P_\gamma$. D2: $^1$H NMR δ (ppm): 9.01 (1H, s, H8 m$^7$G); 8.03 (1H, s, H8G); 5.94 (1H, d, J=2.7 Hz, H1' m$^7$G); 5.79 (1H, d, J=6.1 Hz, G); 4.68 (1H, ~t, H2' G); 4.56 (1H, ~t, H3' m$^7$G); 4.50 (1H, ~t, H3' G); 4.41 (1H, m, H5' G), 4.32 (3H, overlapped m, H4'G, H5"G; 4.26 (3H, overlapped m, H4' m$^7$G, H5' m$^7$G, H5" m$^7$G); 4.07 (3H, s, N—CH$_3$); 3.58 (3H, s, O—CH$_3$), 0.45 (3H, m, BH$_3$). $^{31}$P NMR δ (ppm): 17.4 (1P, ~t, J=29.6 Hz, $P_\beta$ ($P_{BH3}$)), −12.4 (2P, ~d, J=29.6 Hz, $P_\alpha$ and $P_\gamma$).

Example 16

7-methylguanosine 5'-O—(H-phosphonate)

To guanosine 5'-O—(H-phosphonate) (260 mg, 0.65 mmol) dissolved in DMSO (10 ml) was added methyl iodide (322 μl, 5.2 mmol), and the solution was stirred in a stoppered flask for 3 h. The reaction was quenched by diluting with 200 ml of water, and the reaction mixture was extracted three times with ether. The remaining ether was removed from the aqueous layer under reduced pressure, and the product was isolated on DEAE Sephadex with a 0-0.7 M gradient of TEAB. After evaporation and drying over P$_2$O$_5$, 200 mg (0.43 mmol) of product were obtained as a triethylammonium salt (66%). ESI MS (−) m/z: 360.06 (calc for C$_{11}$H$_{15}$N$_5$O$_7$P$_1$ 360.07).

Example 17

7-methylguanosine 5'-O-phosphoroselenoate (m$^7$GMPSe, Triethylammonium Salt)

7-methylguanosine 5'-(H-phosphonate) (200 mg, 0.43 mmol) was placed in a round-bottom flask and suspended in 20 ml of dry acetonitrile. The flask was sealed with a rubber septum and flushed with argon for 30 min. Then N,O-bistrimethylsilylacetamide (11.3 ml, 46 mmol) was injected through a syringe. The mixture was vigorously stirred until a clear solution was obtained, and was then stirred for an additional 30 min. Selenium (40 mg, 0.5 mmol) in pyridine (0.5 ml) was then added, and stirring continued for another 30 min. The solution was evaporated under reduced pressure to an oily residue, a solution of triethylamine (60 μl, 0.43 mmol) in methanol (40 ml) was added, and the resulting mixture was stirred for 2 h. The solution was evaporated and the product was dissolved in 100 ml of water and filtered through a paper filter. The product was isolated on DEAE Sephadex with a 0-0.9 M gradient of TEAB. The fractions after evaporation and freeze-drying yielded 93 mg of 7-methylguanosine 5'-O-phosphoroselenoate triethylammonium salt (45%). ESI MS (−) m/z: 439.97 (calc for C$_{11}$H$_{15}$N$_5$O$_7$P$^{80}$Se 439.98).

Example 18 m$^7$Gp$_{Se}$ppG

To a suspension of m$^7$GMPSe (10 mg, 0.021 mmol) and GDP-Im (15 mg, 0.027 mmol) in DMF (0.8 ml) was added anhydrous ZnCl$_2$ (30 mg, 0.22 mmol). The reaction was maintained at room temperature for 2 days, and was then quenched by adding 90 mg of disodium EDTA in 10 ml of water, and neutralized with solid NaHCO$_3$. The diastereomers were separated by RP HPLC. Yields were 2 mg of m$^7$Gp$_{Se}$ppG (D1) and 2.5 mg of m$^7$Gp$_{Se}$ppG (D2) as NH$_4^+$ salts (10% and 13%, respectively). ESI MS (−) m/z: 865.02 (calc for C$_{21}$H$_{28}$N$_{10}$O$_{17}$P$_3$$^{80}$Se 865.00).

Example 19

Measuring Binding Affinities to eIF4E

Fluorescence titration measurements were carried out on an LS-50B or LS-55 spectrofluorometer (Perkin Elmer Co.) at 20.0±0.2° C. in 50 mM HEPES/KOH (pH 7.2), 0.5 mM EDTA, and 1 mM DTT, with ionic strength adjusted to 150 mM by addition of KCl. Various cap analogue solutions, of increasing concentration, were added in 1 μl aliquots to 1.4 ml of 0.1 or 0.2 μM protein solutions. Fluorescence intensities were measured with excitation at 280 nm or 295 nm with 2.2 nm bandwidth, and detection at 337 nm with 4 nm bandwidth and a 290-nm cut-off filter. The data were corrected for sample dilution and inner filter effects. Equilibrium association constants ($K_{as}$) were determined by fitting the theoretical dependence of fluorescence intensity on cap analog concentration to the experimental data, as otherwise described in A. Niedźwiecka et al., "Biophysical studies of eIF4E cap-binding protein: recognition of mRNA 5' cap structure and synthetic fragments of eIF4G and 4E-BP1 proteins," *J. Mol. Biol.*, vol. 312, pp. 615-635 (2002). The concentration of protein was allowed to be a free parameter in the equilibrium equation, to determine the amount of "active" protein. The final $K_{as}$ was calculated as a weighted average of three to ten independent titrations, with the weights taken as the reciprocals of the squares of the numerical standard deviations. Numerical nonlinear least-square regression analysis was performed using ORGIN 6.0 (Microcal Software Inc., USA).

Example 20

Assay of Susceptibility to DcpS

Human DcpS was expressed in *Escherichia coli* as described in L. Cohen et al., "Nematode m$^7$GpppG and m$_3^{2,2,7}$GpppG decapping: activities in *Ascaris* embryos and characterization of *C. elegans* scavenger DcpS," *RNA*, vol. 10, pp. 1609-1624 (2004). A 15 μM solution of the protein in 20 mM Tris buffer, pH 7.5, containing 50 mM KCl, 0.2 mM EDTA, 1 mM DTT, 0.5 mM PMSF, and 20% glycerol was stored at −80° C. until used. Enzymatic reactions were carried out at 30° C. in 500 μl of 50 mM Tris-HCl, pH 7.9, containing 20 mM MgCl$_2$ and 60 mM (NH$_4$)$_2$SO$_4$. A 40 μM solution of the selected cap analog was treated with 5.0 μl of DcpS for 120 min. At times of 10, 30, 60, and 120 min, a 100-μl sample was collected from the reaction mixture and deactivated by incubation at 90° C. for 2 min. Samples were analyzed without further treatment by analytical RP HPLC with a linear gradient of methanol in 0.1 M KH$_2$PO$_4$, pH 6.0, from 0-50% over 15 min.

Example 21

Synthesis of mRNAs Capped with BH$_3$ and Se-Analogs Method I (for Analogs m$^7$Gpp$_{BH3}$pG (D1/D2 Mix) and m$^7$Gpp$_{BH3}$Pm$^7$G)

A DNA template for in vitro transcription was synthesized by PCR from the plasmid SP6p-5'UTR β-globin-LUCiferase.

The template contained the SP6 promoter followed by the 5'-UTR sequence of rabbit β-globin mRNA and the entire firefly luciferase mRNA coding region. A typical in vitro transcription reaction mixture (50 µl) contained SP6 transcription buffer (Fermentas, cat. no. EP0131), 2 µg of DNA template, 2 U/µl RiboLock Ribonuclease Inhibitor (Fermentas), 2 mM each of ATP, CTP, and UTP, 0.1 mM GTP, and 1 mM dinucleotide cap analog. The reaction mixture was incubated at 37° C. for 5 min before the addition of SP6 RNA polymerase (Fermentas) to a final concentration of 2 U/µl. After 30 min of incubation at 37° C., GTP was added to a final concentration of 1 mM, and the reaction continued for an additional 90 min. The reaction mixtures were then treated with 1 U of DNase RQ1 (RNAse-free, Promega) per µg of template DNA in transcription buffer at 37° C. for 20 min. RNA transcripts were purified on DEPC-treated Sephadex G-50 spin columns (Pharmacia). The integrity of transcripts was confirmed by electrophoresis on a non-denaturating, 1% agarose gel. Concentrations were determined spectrophotometrically. The transcripts were stored at −80° C. until used.

Example 21

Synthesis of mRNAs Capped with $BH_3$ and Se-Analogs Method II (for Analogs $m_2^{7,2'-O}Gpp_{BH3}pG$ (D1), $m_2^{7,2'-O}Gpp_{BH3}pG$ (D2), $m_2^{7,2'-O}Gpp_{BH3}G$ (D1), $m_2^{7,2'-O}Gppp_{BH3}G$ (D2), $m_2^{7,2'-O}Gpp_{Se}pG$ (D1), and $m_2^{7,2'-O}Gpp_{Se}pG$ (D2), $m^7Gpp_{BH3}pG$ (D1), $m^7Gpp_{BH3}pm^7G$, $m_2^{7,2'-O}Gpp_spG$ (D1) and $m_2^{7,2'-O}Gpp_spG$ (D2))

Capped, polyadenylated luciferase mRNAs were synthesized in vitro by PCR from a dsDNA template that contained the SP6 promoter, the 5'-UTR sequence of rabbit β-globin mRNA, the entire firefly luciferase coding region, and 31 adenosine residues. A typical transcription reaction mixture (40 µl) contained SP6 transcription buffer (Fermentas), 0.7 ug of DNA template, 1 U/µl RiboLock Ribonuclease Inhibitor (Fermentas), 0.5 mM each of ATP, CTP, and UTP, 0.1 mM GTP, and 0.5 mM dinucleotide cap analog. The reaction mixture was incubated at 37° C. for 5 min before addition of SP6 RNA polymerase (Fermentas) to a final concentration of 1 U/µl, and incubation then continued for 45 min at 37° C. The reaction mixture was treated with DNase as in Method I. RNA transcripts were purified with NucAway Spin Columns (Ambion). The integrity of transcripts and quantitation was performed as in Method I.

Example 22

Translation Efficiency of Capped mRNAs in an in Vitro System

A micrococcal nuclease-treated rabbit reticulocyte lysate system (Flexi Rabbit Reticulocyte Lysate System, Promega) was used for in vitro translation. Translation reactions were performed in 10 µl for 60 min at 30° C. A typical reaction mixture contained 40% reticulocyte lysate, the 20 "standard" amino acids (0.01 mM each), $MgCl_2$ (1.2 mM), potassium acetate (170 mM), and mRNA (five different concentrations of each transcript, ranging from 0.25 to 4 µg/ml). Luciferase activity was measured in a luminometer (Glomax, Promega). Linear regression was used to fit the data points (luciferase activity versus concentration of mRNA transcript), and translational efficiency was defined as the slope of this line. The relative translational efficiencies of the test mRNAs were compared to that of $m^7GpppG$-capped luciferase mRNA, the latter being defined as 1.0.

Example 23

Inhibition of Cap-Dependent Translation In Vitro by $BH_3$-Analogs

In vitro translation reactions were performed in 12.5 µl for 60 min at 30° C. under conditions favorable for cap-dependent translation. In some cases, the reaction mixture was incubated for 60 min at 30° C. prior to adding the dinucleotide cap analog (inhibitor) and $m_2^{7,3'-O}GppG$-capped luciferase mRNA to start translation. In other cases, to analyze biological stability, the cap analog was incubated in the translation mixture for 60 min at 30° C. prior to adding the luciferase mRNA to start translation. A typical reaction mixture contained 56% reticulocyte lysate, the 20 "standard" amino acids (0.01 mM each), $MgCl_2$ (1.2 mM), potassium acetate (170 mM), RiboLock Ribonuclease Inhibitor (0.32 U/µl), cap analog solution (1/10 of total reaction volume), and $m_2^{7,3'-O}GppG$-capped luciferase RNA. The transcript was not polyadenylated, but instead had a 59-base 3'-UTR. Reactions were performed with cap analog concentrations ranging from 0.12 to 100 µM. Luciferase activity was measured in a luminometer. From the measurements we calculated $IC_{50}$ values, defined as the concentration of cap analog that resulted in 50% inhibition. The program OriginPro8 (OriginLab) was used for curve fitting with the equation $q_{LUC}=Z/(1+I/IC_{50})+N$, where $q_{LUC}$ is the activity of luciferase synthesized in the presence of cap analog, Z is the activity of luciferase synthesized in the absence of cap analog, N is the activity of luciferase synthesized in a cap-independent manner, and I is the cap analog concentration. The data are presented in Table 2.

TABLE 2

Biophysical and biochemical characterization of $BH_3$-analogs

| Cap analog | Cap analog/ eIF4E affinity $(K_{AS})$ µM$^{-1}$ | Susceptibility to DcpS | In vitro translational efficiency | | Inhibition of in vitro translation ($IC_{50}$, µM) | |
|---|---|---|---|---|---|---|
| | | | method I | method II | condition A | condition B |
| $m^7GpppG$ | 9.4 ± 0.4 | hydrolyzed | 1.00 | 1.00 | 8.3 ± 0.2 (n = 21) | 35.1 ± 10.8 |
| $m^7Gpppm^7G$ | 5.0 ± 0.2 | hydrolyzed | N.D. | N.D. | N.D. | N.D. |

TABLE 2-continued

Biophysical and biochemical characterization of BH$_3$-analogs

| Cap analog | Cap analog/ eIF4E affinity ($K_{AS}$) μM$^{-1}$ | Susceptibility to DcpS | In vitro translational efficiency | | Inhibition of in vitro translation (IC$_{50}$, μM) | |
|---|---|---|---|---|---|---|
| | | | method I | method II | condition A | condition B |
| m$^7$Gppp$_{BH3}$G (D1) | 14.5 ± 0.2 | hydrolyzed | N.D. | N.D. | 3.2 ± 0.3 (n = 2) | 9.2 ± 1.9 (n = 2) |
| m$^7$Gppp$_{BH3}$G (D2) | 14.4 ± 0.6 | hydrolyzed | N.D. | N.D. | 3.1 ± 0.2 (n = 2) | 16.4 ± 0.8 (n = 2) |
| m$^7$Gpp$_{BH3}$pG (D1) | 44 ± 2 | resistant | 1.41 ± 0.26 (det. for D1/D2 1:1 mixture) | 1.91 ± 0.37 | 1.6 ± 0.3 (n = 4) | 1.3 ± 0.1 (n = 5) |
| m$^7$Gpp$_{BH3}$pG (D2) | 13.0 ± 0.2 | resistant | N.D. | N.D. | 4.5 ± 0.5 (n = 3) | 3.5 ± 0.9 (n = 3) |
| m$^7$Gpp$_{BH3}$pm$^7$G | 11.1 ± 0.2 | resistant | 2.81 ± 0.16 | 3.56 ± 0.04 | 3.0 ± 0.1 (n = 3) | 3.0 ± 0.2 (n = 4) |
| m$_2^{7,2'\text{-}O}$GpppG | 10.8 ± 0.3 | hydrolyzed | N.D. | N.D. | N.D. | N.D. |
| m$_2^{7,3'\text{-}O}$GpppG | 10.2 ± 0.3 | hydrolyzed | 2.73 ± 0.25 | 1.82 ± 0.20 | N.D. | N.D. |
| m$_2^{7,2'\text{-}O}$Gppp$_{BH3}$G (D1) | 15.3 ± 0.2 | hydrolyzed | N.D. | 2.83 ± 0.63 | N.D. | N.D. |
| m$_2^{7,2'\text{-}O}$Gppp$_{BH3}$G (D2) | 14.4 ± 0.2 | hydrolyzed | N.D. | 1.84 ± 0.11 | N.D. | N.D. |
| m$_2^{7,2'\text{-}O}$Gpp$_{BH3}$pG (D1) | 39.4 ± 1.2 | resistant | N.D. | 2.66 ± 1.11 | N.D. | N.D. |
| m$_2^{7,2'\text{-}O}$Gpp$_{BH3}$pG (D2) | 13.2 ± 0.2 | resistant | N.D. | 3.35 ± 0.26 | N.D. | N.D. |

Example 24

Results of Biophysical and Biochemical Characterization of BH$_3$- and Se-Analogs The binding affinities of eukaryotic eIF4E for various cap analogs were determined by fluorescence quenching. This biophysical test allows one to predict the potential efficacy of cap analogs in translation. Those having higher affinities for eIF4E than the unmodified cap analog (m$^7$GpppG) are expected to be better recognized by the translational machinery, leading to higher translational efficiencies. They also are expected to compete more effectively with unmodified mRNA when free cap dinucleotides are used to inhibit translation. See generally E. Grudzien-Nogalska et al., "Synthesis of anti-reverse cap analogs (ARCAs) and their applications in mRNA translation and stability," *Methods Enzymol.*, vol. 431, pp. 203-227 (2007). The results showed that the association constants for all BH$_3$- and Se-analogs tested were similar to or higher than those of their unmodified counterparts. See Tables 2 and 3.

TABLE 3

Biophysical and biochemical characterization of Se-analogs

| Cap analog | Cap analog-eIF4E affinity ($K_{AS}$) μM$^{-1}$ | Susceptibility to DcpS | In vitro translational efficiency (method II) | Inhibition of in vitro translation (IC$_{50}$, μM) | |
|---|---|---|---|---|---|
| | | | | condition A | condition B |
| m$^7$GpppG | 9.4 ± 0.4 | hydrolyzed | 1.00 | 8.3 ± 0.2 (n = 21) | 35.1 ± 10.8 |
| m$_2^{7,2'\text{-}O}$GpppG | 10.8 ± 0.3 | hydrolyzed | N.D. | N.D. | N.D. |
| m$_2^{7,3'\text{-}O}$GpppG | 10.2 ± 0.3 | hydrolyzed | 1.82 ± 0.20 | N.D. | N.D. |
| m$_2^{7,2'\text{-}O}$Gpp$_{Se}$pG (D1) | 38.5 ± 0.7 | hydrolyzed | 2.24 ± 0.28 | 8.4 ± 1.4 (n = 3) | 14.7 ± 1.6 (n = 1) |
| m$_2^{7,2'\text{-}O}$Gpp$_{Se}$pG (D2) | 19.0 ± 0.5 | hydrolyzed | 2.31 ± 0.22 | 3.9 ± 0.5 (n = 3) | 11.4 ± 7.2 (n = 1) |
| m$^7$Gp$_{Se}$ppG (D1) | N.D. | resistant | N.D. | N.D. | N.D. |
| m$^7$Gp$_{Se}$ppG (D2) | N.D. | resistant | N.D. | N.D. | N.D. |

Example 25

Translational Efficiencies of mRNAs Capped with BH$_3$- and Se-Analogs

Translational efficiencies were determined by in vitro translation. mRNAs capped with the new analogs were generally found to have higher translational efficiencies than mRNAs capped with the unmodified parent compounds (Tables 4 and 5). Particularly high translational efficiencies were observed for analogs that were incorporated into mRNA exclusively in the correct orientation (BH$_3$-ARCAs, Se-ARCAs, and m$^7$Gpp$_{BH3}$pm$^7$G).

TABLE 4

Translational efficiency in vitro of luciferase mRNA capped with modified dinucleotide boranophosphate cap analogs

| | Translation efficiency in comparison with $m^7$GpppG-LUC mRNA | | | | |
|---|---|---|---|---|---|
| | Experiment No. | | | | Mean |
| Cap analog | 1 | 2 | 3 | 4 | (SD) |
| ApppG | 0.34 | 0.55 | 0.53 | 0.48 | 0.48 (0.09) |
| $m^7$GpppG | 1.00 | 1.00 | 1.00 | 1.00 | 1.00 |
| $m_2^{7,3'-O}$GpppG | 2.53 | 2.92 | 2.96 | 2.50 | 2.73 (0.25) |
| $m^7$Gpp$_{BH3}$pG$^a$ | 1.66 | 1.42 | 1.14 | — | 1.41 (0.26) |
| $m^7$Gpp$_{BH3}$p$m^7$G | — | 2.63 | 2.91 | 2.89 | 2.81 (0.16) |

$^a$1:1 mixture of D1 and D2

TABLE 5

In vitro translational efficiency of luciferase mRNA bearing a 31-base poly(A) tail and capped with boranophosphate or phosphoroselenoate cap analogs

| | Translation efficiency in comparison to $m^7$GpppG-LUC-(A)$_{31}$ mRNA | | | | | |
|---|---|---|---|---|---|---|
| | Experiment No. | | | | | Mean |
| Cap analog | 1 | 2 | 3 | 4 | 5 | (SD) |
| ApppG | 0.27 | 0.16 | 0.14 | 0.19 | 0.18 | 0.19 (0.05) |
| $m^7$GpppG | 1.00 | 1.00 | 1.00 | 1.00 | 1.00 | 1.00 |
| $m_2^{7,3'-O}$GpppG | 1.98 | 1.66 | 1.61 | 1.77 | 2.08 | 1.82 (0.20) |
| $m_2^{7,2'-O}$Gpp$_{Se}$pG (D1) | 2.05 | 2.09 | 2.16 | 2.65 | — | 2.24 (0.28) |
| $m_2^{7,2'-O}$Gpp$_{Se}$pG (D2) | 2.53 | 2.31 | 2.09 | — | — | 2.31 (0.22) |
| $m_2^{7,2'-O}$Gpp$_{BH3}$pG (D1) | — | — | — | 1.87 | 3.44 | 2.66 (1.11) |
| $m_2^{7,2'-O}$Gpp$_{BH3}$pG (D2) | — | — | — | 3.16 | 3.53 | 3.35 (0.26) |
| $m^7$Gpp$_{BH3}$pG (D1) | — | — | — | 1.65 | 2.17 | 1.91 (0.37) |
| $m_2^{7,2'-O}$Gppp$_{BH3}$G (D1) | — | — | — | 2.38 | 3.28 | 2.83 (0.63) |
| $m_2^{7,2'-O}$Gppp$_{BH3}$G (D2) | — | — | — | 1.76 | 1.92 | 1.84 (0.11) |
| $m_2^{7,2'-O}$Gpp$_S$pG (D1) | — | — | — | 2.92 | 2.83 | 2.88 (0.06) |
| $m_2^{7,2'-O}$Gpp$_S$pG (D2) | — | — | — | 3.20 | 3.02 | 3.11 (0.13) |
| $m^7$Gpp$_{BH3}$p$m^7$G | — | — | — | — | 3.56 | 3.56 (0.04) |

Example 26

Susceptibility of the New Analogs to Degradation by DcpS was Also Determined

Unexpectedly, it was found that all β-BH$_3$-analogs were resistant to hydrolysis by DcpS (Table 2). Since J. Kowalska et al. (2008) showed that the corresponding β-phosphorothioate cap analogs were all susceptible to DcpS, this result indicates that different phosphate modifications at the same position of the triphosphate bridge can have different biochemical consequences. For Se-analogs, by contrast, only those modified in the γ position were resistant to DcpS (Table 3).

Example 27

The BH$_3$-Analogs as Inhibitors of In Vitro Cap-Dependent Translation

Two type of experiments were carried out. In one set of experiments (condition A), a cap analog was added to the translation system together with luciferase mRNA. In the other set of experiments (condition B), the cap analog was incubated in the translation system for 60 min before addition of mRNA. In both types of experiment, BH$_3$- and Se-analogs were found to be strong inhibitors of translation (Tables 2 and 3). Moreover, in contrast to $m^7$GpppG, incubation of some of these analogs did not impair their inhibitory properties, which is presumably a reflection of their resistance to pyrophosphatase attack. There was a correlation between the resistance to hydrolysis by DcpS and the stability of analogs in the translation system.

Example 28

Measurement of Translational Efficiency and mRNA Decay in Cultured HeLa Cells

Nucleoporation was used to deliver RNA into HeLa cells with a Nucleofector II (Amaxa Biosystems), following the manufacture's recommended protocols. One microgram of RNA was introduced into $10^6$ cells in Nucleofector Solution V, using program T-024.

For measurement of luciferase synthesis, cells were divided into several Eppendorf tubes, placed in a water bath at 37° C., and shaken. For protein extraction, $2 \times 10^5$ cells were lysed in 200 μl of Luciferase Cell Culture Lysis Reagent (Promega). Luciferase activity of cell extracts was measured according to the manufacturer's recommended protocol.

Figure 14:
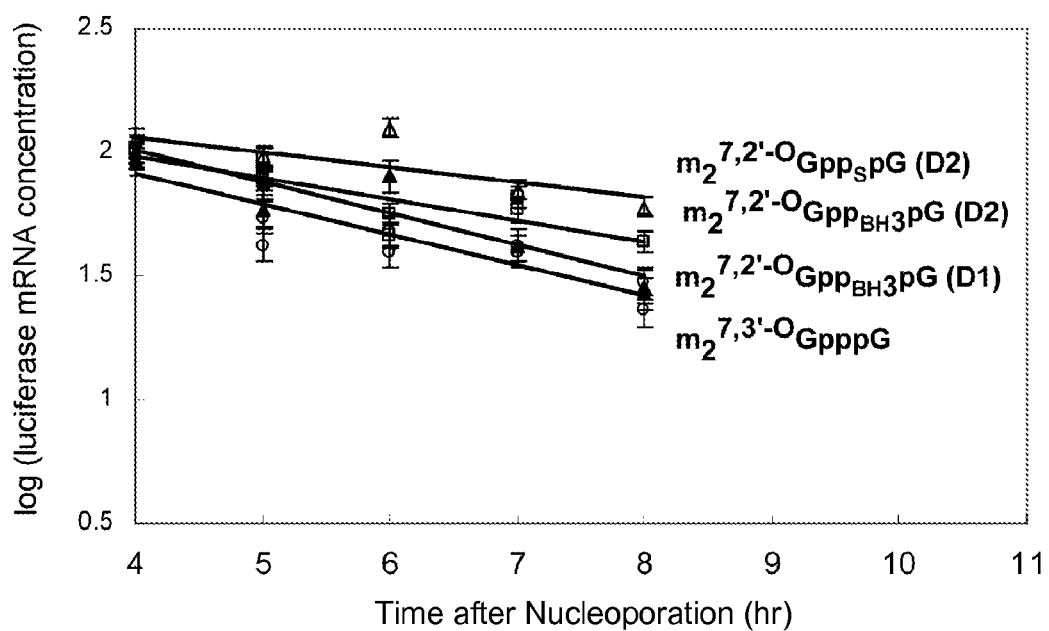
FIG. 14 depicts measurements of the stability of luciferase mRNAs capped with various analogs and having a 60-base poly(A) tail in cultured HeLa cells following nucleoporation.

To measure mRNA stability, cells were distributed into 35-mm cell culture dishes and placed at 37° C. in a 5% CO$_2$, humidified atmosphere. Cells were harvested at various times and washed twice with PBS. For cytoplasmic RNA extraction, 2×10$^5$ cells were lysed in 175 µl of 50 mM Tris-HCl, pH 8.0, 140 mM NaCl, 1.5 mM MgCl$_2$, 0.5% (v/v) Igepal (Sigma), and 1 mM dithiothreitol. RNAs were further purified using the RNeasy® mini kit and analyzed by real-time PCR. Reverse transcription was performed on 400 ng of RNA in 20-µl reaction mixtures containing 5.5 mM MgCl$_2$, 500 µM of each dNTP, 2.5 µM random hexamers, 0.2 units of RNase inhibitor, and 0.8 units of MultiScribe reverse transcriptase (Applied Biosystems). Reaction mixtures were incubated at 25° C. for 10 min, 48° C. for 30 min, and 95° C. for 5 min. Quantitative real-time PCR was performed with specific primers designed for each mRNA with the Beacon Designer tool (Bio-Rad). Luciferase mRNA levels were determined by PCR using primers designed to amplify bases 226-398 from the 5' end. Mouse GAPDH mRNA levels were determined (as control) by the same method and in the same RNA samples using primers specific for mouse GAPDH. Amplification and detection were performed with the iCycler IQ real time PCR detection system in 25-µl reaction mixtures containing 5 µl of the transcription reaction mixture (50 ng of cDNA), 12.5 µl of IQ SYBRgreen Supermix, and 0.3 mM primers (Bio-Rad). The incubation conditions were 3 min at 95° C. for polymerase activation, followed by 40 cycles, each of 15 s at 95° C. and 1 min at 60° C. Luciferase mRNA levels were calculated using the absolute standard curve method as described in User Bulletin No. 2 for the ABI Prism 7700 Sequence Detection System. Luciferase mRNA was then normalized by comparison to the measured level of mouse GAPDH mRNA in each sample, which was an indicator of total cellular RNA purified from a cell extract. Luciferase mRNA remaining at each time point was converted to a percent of the RNA present at zero time, and the results were plotted as log$_{10}$([RNA]) versus time to determine t$_{1/2}$. Results are presented in FIG. 14.

Figure 15:
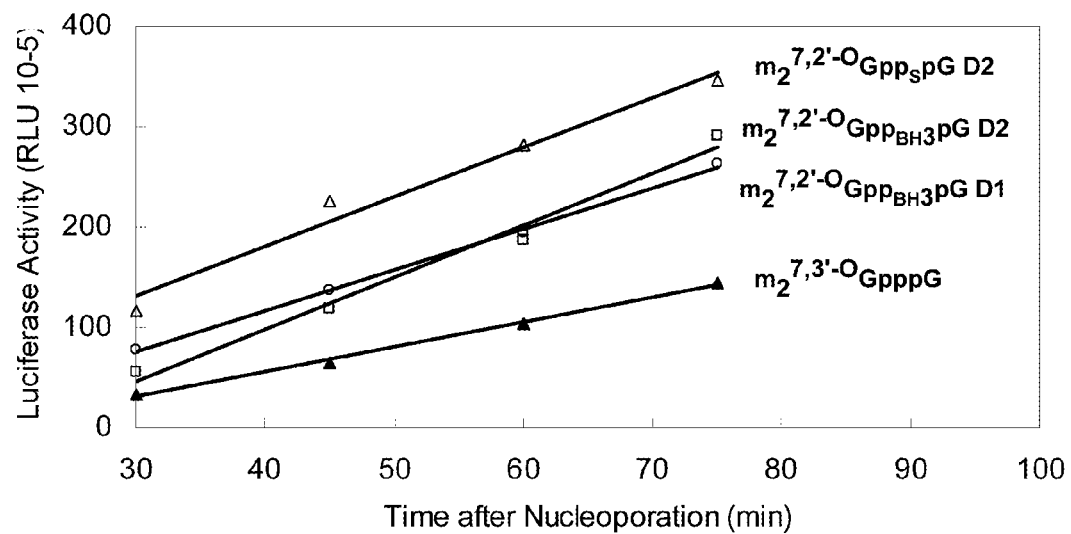
FIG. 15 depicts the translational efficiency of luciferase mRNAs capped with various analogs and bearing a 60-nt poly(A) tail in cultured HeLa cells following nucleoporation.

The translational efficiencies of various luciferase mRNAs were determined by normalizing the rate of luciferase synthesis to the concentration of luciferase mRNA present in cells at zero time. Results are presented in FIG. 15.

Further Examples

Examples of compositions and methods within the scope of the present invention include, but are not limited to, the following:

A composition comprising one or more of the following compounds, or a stereoisomer of one or more of the following compounds, or mixtures of stereoisomers of one or more of the following compounds, or a salt or salts of any of them:

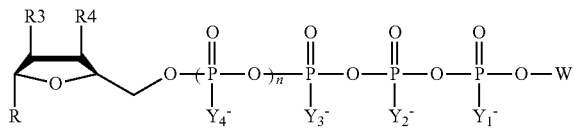

wherein Y$_1$, Y$_2$, Y$_3$, and Y$_4$ are selected from the group consisting of O, BH$_3$, and Se; the various Y$_i$ groups may be the same or different, wherein i is 1, 2, 3, or 4; and at least one Y$_i$ is BH$_3$ or Se;

n is 0 or 1;

R is selected from the group consisting of:

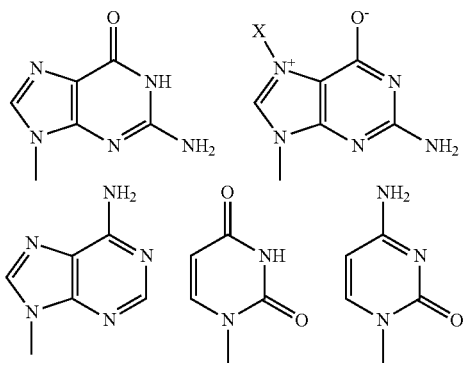

R3 and R4 are selected from the group consisting of H, OH, OCH$_3$ and OCH$_2$CH$_3$; and R3 and R4 may be the same or different;

W is selected from the group consisting of

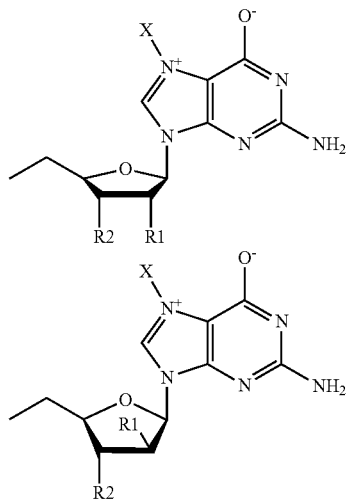

R1 and R2 are selected from the group consisting of H, OH, OCH$_3$, or OCH$_2$CH$_3$; and R1 and R2 may be the same or different; and X is selected from the group consisting of methyl, ethyl, propyl, butyl, benzyl, substituted benzyl, methylenenaphthyl, and substituted methylenenaphthyl.

A composition as described; wherein Y$_1$, Y$_2$, Y$_3$, and Y$_4$ are selected from the group consisting of O and BH$_3$; the various Y$_i$ groups may be the same or different, wherein i is 1, 2, 3, or 4; and at least one Y$_i$ is BH$_3$.

A composition as described, wherein R is selected from the group consisting of

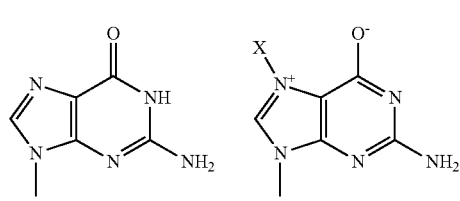

A composition as described, wherein R3 is OH, R4 is OH; and if R is selected from the group consisting of

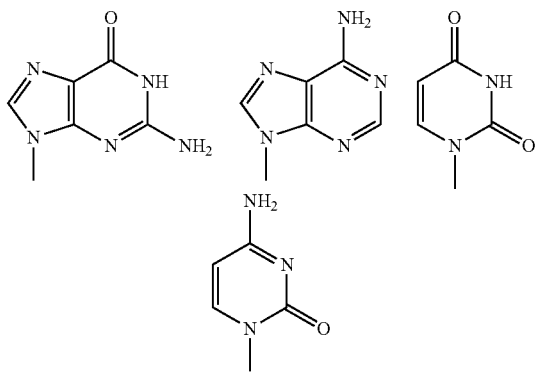

then R1 and R2 are not both OH.

A composition as described, wherein W is

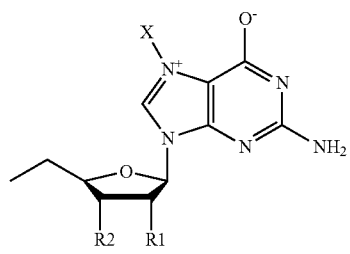

R2 is OH; R1 is H or OCH$_3$; X is methyl; and n=0; and one and only one of Y$_1$, Y$_2$, and Y$_3$ is BH$_3$.

A composition as described; wherein, if n=0, then Y$_2$ or Y$_3$ is BH$_3$; and wherein, if n=1 then Y$_2$, Y$_3$, or Y$_4$ is BH$_3$.

An RNA molecule whose 5' end incorporates a composition as described.

An RNA molecule as described, wherein R is selected from the group consisting of

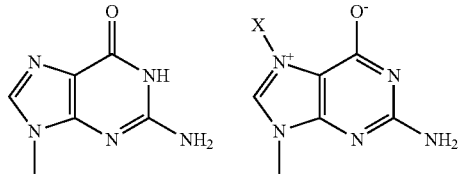

A method of synthesizing, in vitro or in vivo, an RNA molecule as described, said method comprising reacting ATP, CTP, UTP, and GTP, a composition as described, and polynucleotide template in the presence of RNA polymerase, under conditions conductive to transcription by the RNA polymerase of the polynucleotide template into an RNA copy; whereby some of the RNA copies will incorporate the composition to make an RNA molecule as described.

A method for synthesizing a protein or peptide in vitro, said method comprising translating an RNA molecule as described in a cell-free protein synthesis system, wherein the RNA molecule comprises an open reading frame, under conditions conductive to translating the open reading frame of the RNA molecule into the protein or peptide encoded by the open reading frame.

A method for synthesizing a protein or peptide in vivo or in cultured cells, said method comprising translating an RNA molecule as described in vivo or in cultured cells, wherein the RNA molecule comprises an open reading frame, under conditions conductive to translating the open reading frame of the RNA molecule into the protein or peptide encoded by the open reading frame.

A method comprising administering to a system that translates RNA into protein or peptide a composition as described, wherein the amount of the composition administered is effective to wholly or partially inhibit the translation of RNA into protein or peptide.

A method as described, wherein the system is a native RNA translation system of a living organism, and wherein said method comprises the in vivo administration of the composition to the organism.

A composition as described; wherein Y$_1$, Y$_2$, Y$_3$, and Y$_4$ are selected from the group consisting of O and Se; the various Y$_i$ groups may be the same or different, wherein i is 1, 2, 3, or 4; and at least one Y$_i$ is Se.

A composition as described, wherein R is selected from the group consisting of

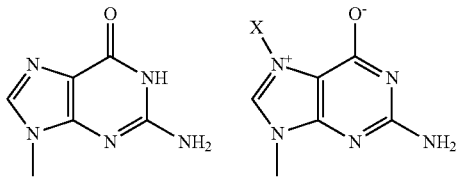

A composition as described, wherein R3 is OH, R4 is OH; and
if R is selected from the group consisting of

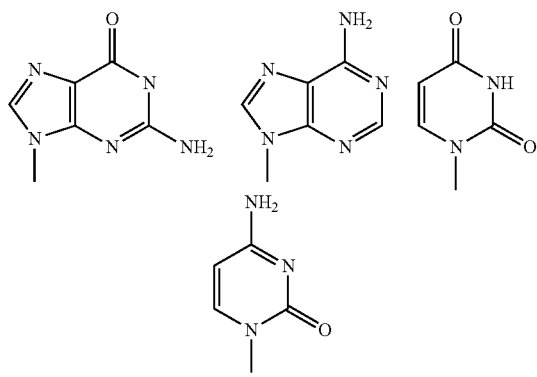

then R1 and R2 are not both OH.

A composition as described, wherein W is

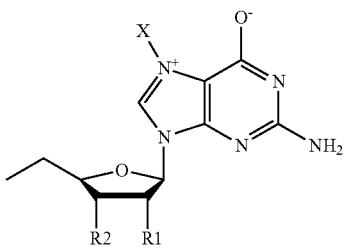

R2 is OH; R1 is H or OCH$_3$; X is methyl; and n=0; and only one of Y$_1$, Y$_2$, and Y$_3$ is Se.

A composition as described; wherein, if n=0, then Y$_2$ or Y$_3$ is Se; and wherein, if n=1 then Y$_2$, Y$_3$, or Y$_4$ is Se.

A composition as described; wherein R1 is OCH$_3$; R2 is OH; R3 is OH; R4 is OH; n is 0; Y$_1$ is O; Y$_2$ is Se; Y$_3$ is O; W is

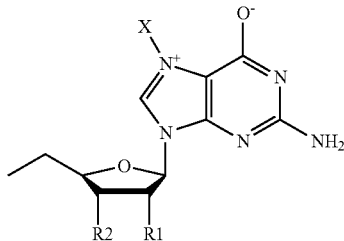

and R is

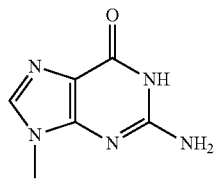

An RNA molecule whose 5' end incorporates a composition as described.

An RNA molecule as described, wherein R is selected from the group consisting of

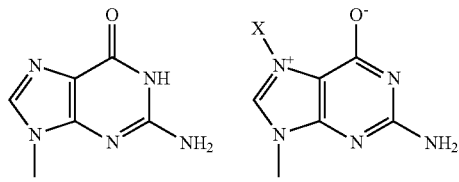

A method of synthesizing, in vitro or in vivo, an RNA molecule as described, said method comprising reacting ATP, CTP, UTP, and GTP, a composition as recited, and polynucleotide template in the presence of RNA polymerase, under conditions conductive to transcription by the RNA polymerase of the polynucleotide template into an RNA copy; whereby some of the RNA copies will incorporate the composition to make an RNA molecule as described.

A method for synthesizing a protein or peptide in vitro, said method comprising translating an RNA molecule as described in a cell-free protein synthesis system, wherein the RNA molecule comprises an open reading frame, under conditions conductive to translating the open reading frame of the RNA molecule into the protein or peptide encoded by the open reading frame.

A method for synthesizing a protein or peptide in vivo or in cultured cells, said method comprising translating an RNA molecule as described in vivo or in cultured cells, wherein the RNA molecule comprises an open reading frame, under conditions conductive to translating the open reading frame of the RNA molecule into the protein or peptide encoded by the open reading frame.

A method comprising administering to a system that translates RNA into protein or peptide a composition as described, wherein the amount of the composition administered is effective to wholly or partially inhibit the translation of RNA into protein or peptide.

A method as described, wherein the system is a native RNA translation system of a living organism, and wherein said method comprises the in vivo administration of the composition to the organism.

The complete disclosures of all references cited in this specification are hereby incorporated by reference. In the event of an otherwise irreconcilable conflict, however, the present specification shall control.

What is claimed is:

1. A composition comprising one or more of the following compounds, or a stereoisomer of one or more of the following compounds, or mixtures of stereoisomers of one or more of the following compounds, or a salt or salts of any of them:

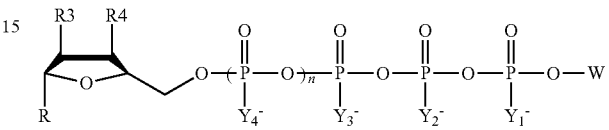

wherein Y$_1$, Y$_2$, Y$_3$, and Y$_4$ are selected from the group consisting of O, BH$_3$, and Se; the various Y$_i$ groups may be the same or different, wherein i is 1, 2, 3, or 4; and at least one Y$_i$ is BH$_3$ or Se;

n is 0 or 1;

R is selected from the group consisting of:

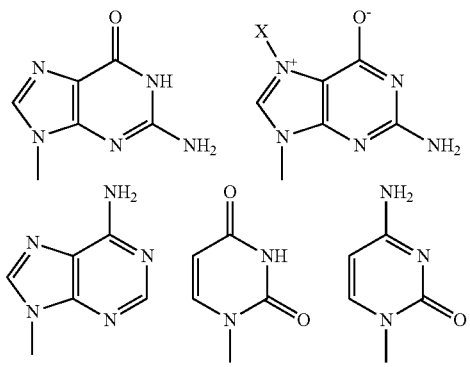

R3 and R4 are selected from the group consisting of H, OH, OCH$_3$ and OCH$_2$CH$_3$; and R3 and R4 may be the same or different;

W is selected from the group consisting of

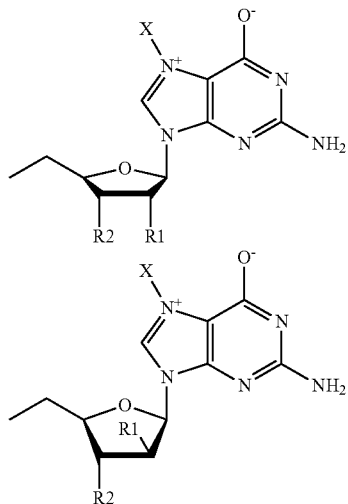

R1 and R2 are selected from the group consisting of H, OH, OCH$_3$, or OCH$_2$CH$_3$; and R1 and R2 may be the same or different; and X is selected from the group consisting of methyl, ethyl, propyl, butyl, benzyl, substituted benzyl, methylenenaphthyl, and substituted methylenenaphthyl.

2. The composition recited in claim 1; wherein $Y_1$, $Y_2$, $Y_3$, and $Y_4$ are selected from the group consisting of O and $BH_3$; the various $Y_i$ groups may be the same or different, wherein i is 1, 2, 3, or 4; and at least one $Y_i$ is $BH_3$.

3. The composition recited in claim 2, wherein R is selected from the group consisting of

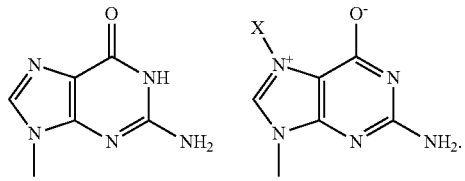

4. The composition recited in claim 2, wherein W is

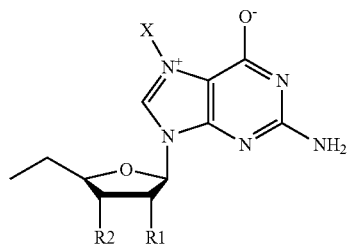

5. The composition recited in claim 2; wherein, if n=0, then $Y_2$ or $Y_3$ is $BH_3$; and wherein, if n=1 then $Y_2$, $Y_3$, or $Y_4$ is $BH_3$.

6. An RNA molecule whose 5' end incorporates the composition recited in claim 2.

7. An RNA molecule whose 5' end incorporates the composition recited in claim 5.

8. The RNA molecule recited in claim 7, wherein R is selected from the group consisting of

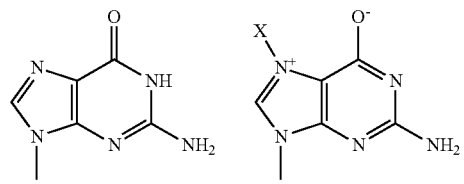

9. A method of synthesizing, in vitro or in vivo, the RNA molecule recited in claim 6, said method comprising reacting ATP, CTP, UTP, and GTP, a composition as recited, and polynucleotide template in the presence of RNA polymerase, under conditions conductive to transcription by the RNA polymerase of the polynucleotide template into an RNA copy; whereby some of the RNA copies will incorporate the composition to make an RNA molecule as recited in claim 6.

10. A method for synthesizing a protein or peptide in vitro, said method comprising translating the RNA molecule recited in claim 6 in a cell-free protein synthesis system, wherein the RNA molecule comprises an open reading frame, under conditions conductive to translating the open reading frame of the RNA molecule into the protein or peptide encoded by the open reading frame.

11. A method for synthesizing a protein or peptide in vivo or in cultured cells, said method comprising translating the RNA molecule recited in claim 6 in vivo or in cultured cells, wherein the RNA molecule comprises an open reading frame, under conditions conductive to translating the open reading frame of the RNA molecule into the protein or peptide encoded by the open reading frame.

12. The composition recited in claim 1; wherein $Y_1$, $Y_2$, $Y_3$, and $Y_4$ are selected from the group consisting of O and Se; the various $Y_i$ groups may be the same or different, wherein i is 1, 2, 3, or 4; and at least one $Y_i$ is Se.

13. The composition recited in claim 12, wherein R is selected from the group consisting of

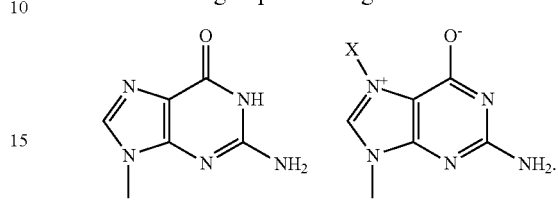

14. The composition recited in claim 13, wherein W is

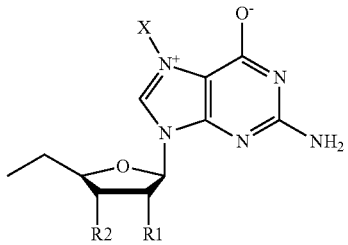

R2 is OH; R1 is H or $OCH_3$; X is methyl; and n=0; and only one of $Y_1$, $Y_2$, and $Y_3$ is Se.

15. The composition recited in claim 12; wherein, if n=0, then $Y_2$ or $Y_3$ is Se; and wherein, if n=1 then $Y_2$, $Y_3$, or $Y_4$ is Se.

16. The composition recited in claim 12; wherein R1 is $OCH_3$; R2 is OH; R3 is OH; R4 is OH; n is 0; $Y_1$ is O; $Y_2$ is Se; $Y_3$ is O; W is

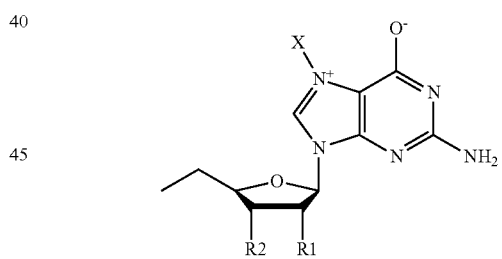

and R is

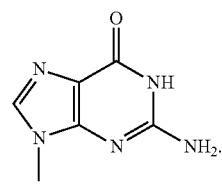

17. An RNA molecule whose 5' end incorporates the composition recited in claim 12.

18. An RNA molecule whose 5' end incorporates the composition recited in claim 13.

19. The RNA molecule recited in claim 18, wherein R is selected from the group consisting of

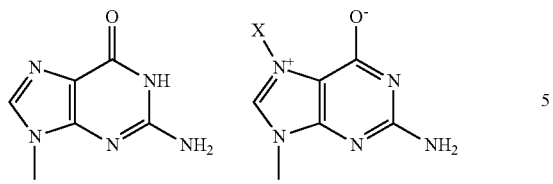

20. A method of synthesizing, in vitro or in vivo, the RNA molecule recited in claim 17, said method comprising reacting ATP, CTP, UTP, and GTP, a composition as recited, and polynucleotide template in the presence of RNA polymerase, under conditions conductive to transcription by the RNA polymerase of the polynucleotide template into an RNA copy; whereby some of the RNA copies will incorporate the composition to make an RNA molecule as recited in claim 17.

21. A method for synthesizing a protein or peptide in vitro, said method comprising translating the RNA molecule recited in claim 17 in a cell-free protein synthesis system, wherein the RNA molecule comprises an open reading frame, under conditions conductive to translating the open reading frame of the RNA molecule into the protein or peptide encoded by the open reading frame.

22. A method for synthesizing a protein or peptide in vivo or in cultured cells, said method comprising translating the RNA molecule recited in claim 17 in vivo or in cultured cells, wherein the RNA molecule comprises an open reading frame, under conditions conductive to translating the open reading frame of the RNA molecule into the protein or peptide encoded by the open reading frame.

\* \* \* \* \*